United States Patent
Laske et al.

(10) Patent No.: US 8,685,077 B2
(45) Date of Patent: Apr. 1, 2014

(54) DELIVERY SYSTEMS AND METHODS OF IMPLANTATION FOR PROSTHETIC HEART VALVES

(75) Inventors: Timothy G. Laske, Shoreview, MN (US); Timothy R. Ryan, Shorewood, MN (US); Carolyn C. Majkrzak, San Clemente, CA (US); Eliot Bloom, Hopkinton, NH (US); Charles Tabor, Shoreview, MN (US)

(73) Assignee: Medtronics, Inc., Minneapolis, MN (US)

( * ) Notice: Subject to any disclaimer, the term of this patent is extended or adjusted under 35 U.S.C. 154(b) by 11 days.

(21) Appl. No.: 13/420,101

(22) Filed: Mar. 14, 2012

(65) Prior Publication Data

US 2012/0197379 A1    Aug. 2, 2012

Related U.S. Application Data

(63) Continuation of application No. 12/357,980, filed on Jan. 22, 2009, now Pat. No. 8,157,853.

(60) Provisional application No. 61/062,207, filed on Jan. 24, 2008.

(51) Int. Cl.
*A61F 2/06* (2013.01)

(52) U.S. Cl.
USPC ........................................... 623/1.11

(58) Field of Classification Search
USPC ........... 623/1.11, 1.23, 1.24, 1.26–1.28, 2.11; 606/200

See application file for complete search history.

(56) References Cited

U.S. PATENT DOCUMENTS

| 3,334,629 A | 8/1967 | Cohn |
|---|---|---|
| 3,409,013 A | 11/1968 | Berry |

(Continued)

FOREIGN PATENT DOCUMENTS

| CN | 2007-100074433 | 8/2007 |
|---|---|---|
| DE | 3640745 | 6/1987 |

(Continued)

OTHER PUBLICATIONS

Andersen, H.R. et al, "Transluminal implantation of artificial heart valves. Description of a new expandable aortic valve and initial results with implantation by catheter technique in closed chest pigs." Euro. Heart J. (1992) 13:704-708.

(Continued)

*Primary Examiner* — Darwin Erezo
*Assistant Examiner* — Erin Colello

(57) ABSTRACT

A delivery system with sequential release mechanism and method of delivering and deploying an implantable stented device into a body lumen including a tabular body, a plurality of activation members extending from the distal end of the tubular body, and a plurality of disks. Each disk includes a proximal and distal surface, at least one stent engagement element attached to the distal surface of the disk and at least one aperture. At least one activation member attaches to the proximal surface of a first disk and at least one activation member passes through an aperture of the first disk and attaches to the proximal surface of a second disk. At least one stent engagement element attached to the distal surface of the first disk passes through an aperture of the second disk. Axially movement of the activation members causes sequential release of the stent engagement elements from a stented device.

23 Claims, 9 Drawing Sheets

(56) References Cited

U.S. PATENT DOCUMENTS

| | | |
|---|---|---|
| 3,540,431 A | 11/1970 | Mobin-Uddin |
| 3,587,115 A | 6/1971 | Shiley |
| 3,628,535 A | 12/1971 | Ostrowsky et al. |
| 3,642,004 A | 2/1972 | Osthagen et al. |
| 3,657,744 A | 4/1972 | Ersek |
| 3,671,979 A | 6/1972 | Moulopoulos |
| 3,714,671 A | 2/1973 | Edwards et al. |
| 3,755,823 A | 9/1973 | Hancock |
| 3,795,246 A | 3/1974 | Sturgeon |
| 3,839,741 A | 10/1974 | Haller |
| 3,868,956 A | 3/1975 | Alfidi et al. |
| 3,874,388 A | 4/1975 | King et al. |
| 4,035,849 A | 7/1977 | Angell et al. |
| 4,056,854 A | 11/1977 | Boretos et al. |
| 4,106,129 A | 8/1978 | Carpentier et al. |
| 4,222,126 A | 9/1980 | Boretos et al. |
| 4,233,690 A | 11/1980 | Akins |
| 4,265,694 A | 5/1981 | Boretos |
| 4,291,420 A | 9/1981 | Reul |
| 4,297,749 A | 11/1981 | Davis et al. |
| 4,339,831 A | 7/1982 | Johnson |
| 4,343,048 A | 8/1982 | Ross et al. |
| 4,345,340 A | 8/1982 | Rosen |
| 4,425,908 A | 1/1984 | Simon |
| 4,470,157 A | 9/1984 | Love |
| 4,501,030 A | 2/1985 | Lane |
| 4,506,394 A | 3/1985 | Bedard |
| 4,574,803 A | 3/1986 | Storz |
| 4,580,568 A | 4/1986 | Gianturco |
| 4,592,340 A | 6/1986 | Boyles |
| 4,610,688 A | 9/1986 | Silvestrini et al. |
| 4,612,011 A | 9/1986 | Kautzky |
| 4,647,283 A | 3/1987 | Carpentier et al. |
| 4,648,881 A | 3/1987 | Carpentier et al. |
| 4,655,771 A | 4/1987 | Wallsten |
| 4,662,885 A | 5/1987 | DiPisa, Jr. |
| 4,665,906 A | 5/1987 | Jervis |
| 4,681,908 A | 7/1987 | Broderick et al. |
| 4,710,192 A | 12/1987 | Liotta et al. |
| 4,733,665 A | 3/1988 | Palmaz |
| 4,777,951 A | 10/1988 | Cribier et al. |
| 4,787,899 A | 11/1988 | Lazarus |
| 4,787,901 A | 11/1988 | Baykut |
| 4,796,629 A | 1/1989 | Grayzel |
| 4,819,751 A | 4/1989 | Shimada et al. |
| 4,834,755 A | 5/1989 | Silvestrini et al. |
| 4,856,516 A | 8/1989 | Hillstead |
| 4,872,874 A | 10/1989 | Taheri |
| 4,878,495 A | 11/1989 | Grayzel |
| 4,878,906 A | 11/1989 | Lindemann et al. |
| 4,883,458 A | 11/1989 | Shiber |
| 4,909,252 A | 3/1990 | Goldberger |
| 4,913,141 A | 4/1990 | Hillstead |
| 4,917,102 A | 4/1990 | Miller et al. |
| 4,922,905 A | 5/1990 | Strecker |
| 4,954,126 A | 9/1990 | Wallsten |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 5,002,559 A | 3/1991 | Tower |
| 5,007,896 A | 4/1991 | Shiber |
| 5,026,366 A | 6/1991 | Leckrone |
| 5,032,128 A | 7/1991 | Alonso |
| 5,037,434 A | 8/1991 | Lane |
| 5,047,041 A | 9/1991 | Samuels |
| 5,059,177 A | 10/1991 | Towne et al. |
| 5,061,273 A | 10/1991 | Yock |
| 5,085,635 A | 2/1992 | Cragg |
| 5,089,015 A | 2/1992 | Ross |
| 5,152,771 A | 10/1992 | Sabbaghian et al. |
| 5,161,547 A | 11/1992 | Tower |
| 5,163,953 A | 11/1992 | Vince |
| 5,167,628 A | 12/1992 | Boyles |
| 5,217,483 A | 6/1993 | Tower |
| 5,232,445 A | 8/1993 | Bonzel |
| 5,272,909 A | 12/1993 | Nguyen et al. |
| 5,295,958 A | 3/1994 | Shturman |
| 5,327,774 A | 7/1994 | Nguyen et al. |
| 5,332,402 A | 7/1994 | Teitelbaum et al. |
| 5,350,398 A | 9/1994 | Pavcnik et al. |
| 5,370,685 A | 12/1994 | Stevens |
| 5,389,106 A | 2/1995 | Tower |
| 5,397,351 A | 3/1995 | Pavcnik et al. |
| 5,411,552 A | 5/1995 | Andersen et al. |
| 5,415,633 A | 5/1995 | Lazarus et al. |
| 5,431,676 A | 7/1995 | Dubrul et al. |
| 5,433,723 A | 7/1995 | Lindenberg et al. |
| 5,443,446 A | 8/1995 | Shturman |
| 5,443,477 A * | 8/1995 | Marin et al. .................. 606/198 |
| 5,443,500 A | 8/1995 | Sigwart |
| 5,449,384 A | 9/1995 | Johnson |
| 5,480,424 A | 1/1996 | Cox |
| 5,489,294 A | 2/1996 | McVenes et al. |
| 5,489,297 A | 2/1996 | Duran |
| 5,496,346 A | 3/1996 | Horzewski et al. |
| 5,500,014 A | 3/1996 | Quijano et al. |
| 5,507,767 A | 4/1996 | Maeda et al. |
| 5,545,209 A | 8/1996 | Roberts et al. |
| 5,545,211 A | 8/1996 | An et al. |
| 5,545,214 A | 8/1996 | Stevens |
| 5,554,185 A | 9/1996 | Block et al. |
| 5,575,818 A | 11/1996 | Pinchuk |
| 5,580,922 A | 12/1996 | Park et al. |
| 5,591,195 A | 1/1997 | Taheri et al. |
| 5,609,626 A | 3/1997 | Quijano et al. |
| 5,645,559 A | 7/1997 | Hachtman et al. |
| 5,665,115 A | 9/1997 | Cragg |
| 5,667,523 A | 9/1997 | Bynon et al. |
| 5,674,277 A | 10/1997 | Freitag |
| 5,695,498 A | 12/1997 | Tower |
| 5,702,368 A | 12/1997 | Stevens et al. |
| 5,713,953 A | 2/1998 | Vallana et al. |
| 5,716,417 A | 2/1998 | Girard et al. |
| 5,746,709 A | 5/1998 | Rom et al. |
| 5,749,890 A | 5/1998 | Shaknovich |
| 5,749,921 A | 5/1998 | Lenker et al. |
| 5,766,151 A | 6/1998 | Valley et al. |
| 5,776,142 A | 7/1998 | Gunderson |
| 5,782,809 A | 7/1998 | Umeno et al. |
| 5,800,455 A | 9/1998 | Palermo et al. |
| 5,800,456 A | 9/1998 | Maeda et al. |
| 5,800,508 A | 9/1998 | Goicoechea et al. |
| 5,807,405 A * | 9/1998 | Vanney et al. ............... 623/2.11 |
| 5,817,126 A | 10/1998 | Imran |
| 5,824,041 A | 10/1998 | Lenker et al. |
| 5,824,043 A | 10/1998 | Cottone, Jr. |
| 5,824,053 A | 10/1998 | Khosravi et al. |
| 5,824,056 A | 10/1998 | Rosenberg |
| 5,824,061 A | 10/1998 | Quijano et al. |
| 5,824,064 A | 10/1998 | Taheri |
| 5,840,081 A | 11/1998 | Andersen et al. |
| 5,843,158 A | 12/1998 | Lenker et al. |
| 5,851,232 A | 12/1998 | Lois |
| 5,855,597 A | 1/1999 | Jayaraman |
| 5,855,601 A | 1/1999 | Bessler et al. |
| 5,860,966 A | 1/1999 | Tower |
| 5,861,028 A | 1/1999 | Angell |
| 5,868,783 A | 2/1999 | Tower |
| 5,876,448 A | 3/1999 | Thompson et al. |
| 5,888,201 A | 3/1999 | Stinson et al. |
| 5,891,191 A | 4/1999 | Stinson |
| 5,906,619 A | 5/1999 | Olson et al. |
| 5,907,893 A | 6/1999 | Zadno-Azizi et al. |
| 5,913,842 A | 6/1999 | Boyd et al. |
| 5,925,063 A | 7/1999 | Khosravi |
| 5,944,738 A | 8/1999 | Amplatz et al. |
| 5,957,949 A | 9/1999 | Leonhardt et al. |
| 5,968,068 A | 10/1999 | Dehdashtian et al. |
| 5,984,957 A | 11/1999 | Laptewicz, Jr. et al. |
| 5,997,573 A | 12/1999 | Quijano et al. |
| 6,022,370 A | 2/2000 | Tower |
| 6,027,525 A | 2/2000 | Suh et al. |
| 6,029,671 A | 2/2000 | Stevens et al. |

(56) References Cited

U.S. PATENT DOCUMENTS

| | | |
|---|---|---|
| 6,042,589 A | 3/2000 | Marianne |
| 6,042,598 A | 3/2000 | Tsugita et al. |
| 6,042,607 A | 3/2000 | Williamson, IV |
| 6,051,014 A | 4/2000 | Jang |
| 6,059,809 A | 5/2000 | Amor et al. |
| 6,110,201 A | 8/2000 | Quijano et al. |
| 6,146,366 A | 11/2000 | Schachar |
| 6,159,239 A | 12/2000 | Greenhalgh |
| 6,162,208 A | 12/2000 | Hipps |
| 6,162,245 A | 12/2000 | Jayaraman |
| 6,168,614 B1 | 1/2001 | Andersen et al. |
| 6,168,616 B1 | 1/2001 | Brown, III |
| 6,168,618 B1 | 1/2001 | Frantzen |
| 6,171,335 B1 | 1/2001 | Wheatley et al. |
| 6,200,336 B1 | 3/2001 | Pavcnik et al. |
| 6,203,550 B1 | 3/2001 | Olson |
| 6,210,408 B1 | 4/2001 | Chandrasekaran et al. |
| 6,218,662 B1 | 4/2001 | Tchakarov et al. |
| 6,221,006 B1 | 4/2001 | Dubrul et al. |
| 6,221,091 B1 | 4/2001 | Khosravi |
| 6,241,738 B1 | 6/2001 | Dereume |
| 6,241,757 B1 | 6/2001 | An et al. |
| 6,245,102 B1 | 6/2001 | Jayaraman |
| 6,248,116 B1 | 6/2001 | Chevilon |
| 6,258,114 B1 | 7/2001 | Konya et al. |
| 6,258,115 B1 | 7/2001 | Dubrul |
| 6,258,120 B1 | 7/2001 | McKenzie et al. |
| 6,277,555 B1 | 8/2001 | Duran et al. |
| 6,299,637 B1 | 10/2001 | Shaolian et al. |
| 6,302,906 B1 | 10/2001 | Goicoechea et al. |
| 6,309,382 B1 | 10/2001 | Garrison et al. |
| 6,309,417 B1 | 10/2001 | Spence et al. |
| 6,338,735 B1 | 1/2002 | Stevens |
| 6,348,063 B1 | 2/2002 | Yassour et al. |
| 6,350,277 B1 | 2/2002 | Kocur |
| 6,352,708 B1 | 3/2002 | Duran et al. |
| 6,371,970 B1 | 4/2002 | Khosravi et al. |
| 6,371,979 B1 | 4/2002 | Beyar et al. |
| 6,371,983 B1 | 4/2002 | Lane |
| 6,379,383 B1 | 4/2002 | Palmaz et al. |
| 6,380,457 B1 | 4/2002 | Yurek et al. |
| 6,398,807 B1 | 6/2002 | Chouinard et al. |
| 6,409,750 B1 | 6/2002 | Hyodoh et al. |
| 6,425,916 B1 | 7/2002 | Garrison et al. |
| 6,440,164 B1 | 8/2002 | DiMatteo et al. |
| 6,454,799 B1 | 9/2002 | Schreck |
| 6,458,153 B1 | 10/2002 | Bailey et al. |
| 6,461,382 B1 | 10/2002 | Cao |
| 6,468,303 B1 | 10/2002 | Amplatz et al. |
| 6,475,239 B1 | 11/2002 | Campbell et al. |
| 6,482,228 B1 | 11/2002 | Norred |
| 6,488,704 B1 | 12/2002 | Connelly et al. |
| 6,494,909 B2 | 12/2002 | Greenhalgh |
| 6,503,272 B2 | 1/2003 | Duerig et al. |
| 6,508,833 B2 | 1/2003 | Pavcnik et al. |
| 6,517,548 B2 | 2/2003 | Lorentzen Cornelius et al. |
| 6,527,800 B1 | 3/2003 | McGuckin, Jr. et al. |
| 6,530,949 B2 | 3/2003 | Konya et al. |
| 6,530,952 B2 | 3/2003 | Vesely |
| RE38,091 E | 4/2003 | Strecker |
| 6,562,031 B2 | 5/2003 | Chandrasekaran et al. |
| 6,562,058 B2 | 5/2003 | Seguin et al. |
| 6,569,196 B1 | 5/2003 | Vesely |
| 6,582,460 B1 | 6/2003 | Cryer |
| 6,585,758 B1 | 7/2003 | Chouinard et al. |
| 6,592,546 B1 | 7/2003 | Barbut et al. |
| 6,605,104 B2 * | 8/2003 | Sato et al. ............ 606/206 |
| 6,605,112 B1 | 8/2003 | Moll et al. |
| 6,607,539 B1 * | 8/2003 | Hayashi et al. ............ 606/108 |
| 6,613,077 B2 | 9/2003 | Gilligan et al. |
| 6,622,604 B1 | 9/2003 | Chouinard et al. |
| 6,635,068 B1 | 10/2003 | Dubrul et al. |
| 6,635,079 B2 | 10/2003 | Unsworth et al. |
| 6,652,571 B1 | 11/2003 | White et al. |
| 6,652,578 B2 | 11/2003 | Bailey et al. |
| 6,656,213 B2 | 12/2003 | Solem |
| 6,663,663 B2 | 12/2003 | Kim et al. |
| 6,666,881 B1 | 12/2003 | Richter et al. |
| 6,669,724 B2 | 12/2003 | Park et al. |
| 6,673,089 B1 | 1/2004 | Yassour et al. |
| 6,673,109 B2 | 1/2004 | Cox |
| 6,676,698 B2 | 1/2004 | McGuckin, Jr. et al. |
| 6,682,558 B2 | 1/2004 | Tu et al. |
| 6,682,559 B2 | 1/2004 | Myers et al. |
| 6,685,739 B2 | 2/2004 | DiMatteo et al. |
| 6,689,144 B2 | 2/2004 | Gerberding |
| 6,689,164 B1 | 2/2004 | Seguin |
| 6,692,512 B2 | 2/2004 | Jang |
| 6,692,513 B2 | 2/2004 | Streeter et al. |
| 6,695,878 B2 | 2/2004 | McGuckin, Jr. et al. |
| 6,702,851 B1 | 3/2004 | Chinn et al. |
| 6,719,789 B2 | 4/2004 | Cox |
| 6,730,118 B2 | 5/2004 | Spenser et al. |
| 6,730,377 B2 | 5/2004 | Wang |
| 6,733,525 B2 | 5/2004 | Yang et al. |
| 6,736,846 B2 | 5/2004 | Cox |
| 6,752,828 B2 | 6/2004 | Thornton |
| 6,758,855 B2 | 7/2004 | Fulton, III et al. |
| 6,769,434 B2 | 8/2004 | Liddicoat et al. |
| 6,776,791 B1 | 8/2004 | Stallings et al. |
| 6,786,925 B1 | 9/2004 | Schoon et al. |
| 6,790,229 B1 | 9/2004 | Berreklouw |
| 6,790,230 B2 | 9/2004 | Beyersdorf et al. |
| 6,792,979 B2 | 9/2004 | Konya et al. |
| 6,797,002 B2 | 9/2004 | Spence et al. |
| 6,821,297 B2 | 11/2004 | Snyders |
| 6,830,575 B2 | 12/2004 | Stenzel et al. |
| 6,830,584 B1 | 12/2004 | Seguin |
| 6,830,585 B1 | 12/2004 | Artof |
| 6,846,325 B2 | 1/2005 | Liddicoat |
| 6,866,650 B2 | 3/2005 | Stevens |
| 6,872,223 B2 | 3/2005 | Roberts |
| 6,875,231 B2 | 4/2005 | Anduiza et al. |
| 6,883,522 B2 | 4/2005 | Spence et al. |
| 6,887,266 B2 | 5/2005 | Williams et al. |
| 6,890,330 B2 | 5/2005 | Streeter et al. |
| 6,893,460 B2 | 5/2005 | Spenser et al. |
| 6,896,690 B1 | 5/2005 | Lambrecht et al. |
| 6,908,481 B2 | 6/2005 | Cribier |
| 6,913,600 B2 | 7/2005 | Valley et al. |
| 6,929,653 B2 | 8/2005 | Strecter |
| 6,936,066 B2 | 8/2005 | Palmaz et al. |
| 6,939,365 B1 | 9/2005 | Fogarty et al. |
| 6,951,571 B1 | 10/2005 | Srivastava |
| 6,974,474 B2 | 12/2005 | Pavcnik et al. |
| 6,974,476 B2 | 12/2005 | McGuckin et al. |
| 6,986,742 B2 | 1/2006 | Hart et al. |
| 6,989,027 B2 | 1/2006 | Allen et al. |
| 6,989,028 B2 | 1/2006 | Lashinski et al. |
| 6,991,649 B2 | 1/2006 | Sievers |
| 7,018,401 B1 | 3/2006 | Hyodoh et al. |
| 7,022,132 B2 | 4/2006 | Kocur |
| 7,041,128 B2 | 5/2006 | McGuckin, Jr. et al. |
| 7,044,966 B2 | 5/2006 | Svanidze et al. |
| 7,048,014 B2 | 5/2006 | Hyodoh et al. |
| 7,097,659 B2 | 8/2006 | Woolfson et al. |
| 7,101,396 B2 | 9/2006 | Artof et al. |
| 7,105,016 B2 | 9/2006 | Shiu et al. |
| 7,115,141 B2 | 10/2006 | Menz et al. |
| 7,128,759 B2 | 10/2006 | Osborne et al. |
| 7,147,663 B1 | 12/2006 | Berg et al. |
| 7,153,324 B2 | 12/2006 | Case et al. |
| 7,160,319 B2 | 1/2007 | Chouinard et al. |
| 7,175,656 B2 | 2/2007 | Khairkhahan |
| 7,186,265 B2 | 3/2007 | Sharkawy et al. |
| 7,195,641 B2 | 3/2007 | Palmaz et al. |
| 7,198,646 B2 | 4/2007 | Figulla et al. |
| 7,201,761 B2 | 4/2007 | Woolfson et al. |
| 7,201,772 B2 | 4/2007 | Schwammenthal et al. |
| 7,252,680 B2 | 8/2007 | Freitag |
| 7,252,682 B2 | 8/2007 | Seguin |
| 7,300,457 B2 | 11/2007 | Palmaz |
| 7,300,463 B2 | 11/2007 | Liddicoat |
| 7,316,706 B2 | 1/2008 | Bloom et al. |

(56) References Cited

U.S. PATENT DOCUMENTS

| | | | |
|---|---|---|---|
| 7,329,278 B2 | 2/2008 | Seguin | |
| 7,335,218 B2 | 2/2008 | Wilson et al. | |
| 7,338,520 B2 | 3/2008 | Bailey et al. | |
| 7,374,571 B2 | 5/2008 | Pease et al. | |
| 7,377,938 B2 | 5/2008 | Sarac et al. | |
| 7,381,218 B2 | 6/2008 | Schreck | |
| 7,384,411 B1 | 6/2008 | Condado | |
| 7,429,269 B2 | 9/2008 | Schwammenthal et al. | |
| 7,442,204 B2 | 10/2008 | Schwammenthal et al. | |
| 7,462,191 B2 | 12/2008 | Spenser et al. | |
| 7,470,284 B2 | 12/2008 | Lambrecht et al. | |
| 7,481,838 B2 | 1/2009 | Carpentier et al. | |
| 7,544,206 B2 | 6/2009 | Cohn et al. | |
| 7,547,322 B2 | 6/2009 | Sarac et al. | |
| 7,556,646 B2 | 7/2009 | Yang et al. | |
| 7,615,067 B2 * | 11/2009 | Lee et al. | 606/205 |
| 7,651,521 B2 | 1/2010 | Ton et al. | |
| 7,682,390 B2 | 3/2010 | Seguin | |
| 7,712,606 B2 * | 5/2010 | Salahieh et al. | 206/210 |
| 7,722,666 B2 * | 5/2010 | Lafontaine | 623/2.11 |
| 7,771,463 B2 | 8/2010 | Ton et al. | |
| 7,780,726 B2 | 8/2010 | Seguin | |
| 7,785,361 B2 | 8/2010 | Nikolchev et al. | |
| 7,806,919 B2 | 10/2010 | Bloom et al. | |
| 7,824,442 B2 * | 11/2010 | Salahieh et al. | 623/2.11 |
| 7,824,443 B2 * | 11/2010 | Salahieh et al. | 623/2.11 |
| 7,837,643 B2 | 11/2010 | Levine et al. | |
| 7,862,602 B2 * | 1/2011 | Licata et al. | 623/1.11 |
| 8,136,659 B2 * | 3/2012 | Salahieh et al. | 206/210 |
| 8,157,852 B2 * | 4/2012 | Bloom et al. | 623/1.11 |
| 8,157,853 B2 * | 4/2012 | Laske et al. | 623/1.11 |
| 8,287,584 B2 * | 10/2012 | Salahieh et al. | 623/1.11 |
| 8,328,868 B2 * | 12/2012 | Paul et al. | 623/2.11 |
| 2001/0001314 A1 | 5/2001 | Davison et al. | |
| 2001/0002445 A1 | 5/2001 | Vesely | |
| 2001/0007956 A1 | 7/2001 | Letac et al. | |
| 2001/0010017 A1 | 7/2001 | Letac et al. | |
| 2001/0011189 A1 | 8/2001 | Drasler et al. | |
| 2001/0021872 A1 | 9/2001 | Bailey et al. | |
| 2001/0025196 A1 | 9/2001 | Chinn et al. | |
| 2001/0032013 A1 | 10/2001 | Marton | |
| 2001/0037142 A1 | 11/2001 | Stelter et al. | |
| 2001/0039450 A1 | 11/2001 | Pavcnik et al. | |
| 2001/0041928 A1 | 11/2001 | Pavcnik et al. | |
| 2001/0044647 A1 | 11/2001 | Pinchuk et al. | |
| 2001/0047150 A1 | 11/2001 | Chobotov | |
| 2001/0049550 A1 | 12/2001 | Martin et al. | |
| 2002/0010508 A1 | 1/2002 | Chobotov | |
| 2002/0029014 A1 | 3/2002 | Jayaraman | |
| 2002/0032480 A1 | 3/2002 | Spence et al. | |
| 2002/0032481 A1 | 3/2002 | Gabbay | |
| 2002/0035396 A1 | 3/2002 | Heath | |
| 2002/0042650 A1 | 4/2002 | Vardi et al. | |
| 2002/0052651 A1 | 5/2002 | Myers et al. | |
| 2002/0058995 A1 | 5/2002 | Stevens | |
| 2002/0065545 A1 | 5/2002 | Leonhardt et al. | |
| 2002/0072789 A1 | 6/2002 | Hackett et al. | |
| 2002/0091439 A1 | 7/2002 | Baker et al. | |
| 2002/0095209 A1 | 7/2002 | Zadno-Azizi et al. | |
| 2002/0099439 A1 | 7/2002 | Schwartz et al. | |
| 2002/0103533 A1 | 8/2002 | Langberg et al. | |
| 2002/0107565 A1 | 8/2002 | Greenhalgh | |
| 2002/0111674 A1 | 8/2002 | Chouinard et al. | |
| 2002/0120277 A1 | 8/2002 | Hauschild et al. | |
| 2002/0120323 A1 | 8/2002 | Thompson et al. | |
| 2002/0123802 A1 | 9/2002 | Snyders | |
| 2002/0133183 A1 | 9/2002 | Lentz et al. | |
| 2002/0138138 A1 | 9/2002 | Yang | |
| 2002/0151956 A1 * | 10/2002 | Chobotov et al. | 623/1.12 |
| 2002/0151970 A1 | 10/2002 | Garrison et al. | |
| 2002/0161392 A1 | 10/2002 | Dubrul | |
| 2002/0161394 A1 | 10/2002 | Macoviak et al. | |
| 2002/0188341 A1 | 12/2002 | Elliott | |
| 2002/0193871 A1 | 12/2002 | Beyersdorf et al. | |
| 2003/0004560 A1 | 1/2003 | Chobotov et al. | |
| 2003/0014104 A1 | 1/2003 | Cribier | |
| 2003/0023300 A1 | 1/2003 | Bailey et al. | |
| 2003/0023303 A1 | 1/2003 | Palmaz et al. | |
| 2003/0028247 A1 | 2/2003 | Cali | |
| 2003/0036791 A1 | 2/2003 | Bonhoeffer et al. | |
| 2003/0040771 A1 | 2/2003 | Hyodoh et al. | |
| 2003/0040772 A1 | 2/2003 | Hyodoh et al. | |
| 2003/0040792 A1 | 2/2003 | Gabbay | |
| 2003/0050684 A1 | 3/2003 | Abrams et al. | |
| 2003/0050694 A1 | 3/2003 | Yang et al. | |
| 2003/0055495 A1 | 3/2003 | Pease et al. | |
| 2003/0065386 A1 | 4/2003 | Weadock | |
| 2003/0069492 A1 | 4/2003 | Abrams et al. | |
| 2003/0109924 A1 | 6/2003 | Cribier | |
| 2003/0125795 A1 | 7/2003 | Pavcnik et al. | |
| 2003/0130726 A1 | 7/2003 | Thorpe et al. | |
| 2003/0130729 A1 | 7/2003 | Paniagua et al. | |
| 2003/0135257 A1 | 7/2003 | Taheri | |
| 2003/0139804 A1 | 7/2003 | Hankh et al. | |
| 2003/0149475 A1 | 8/2003 | Hyodoh et al. | |
| 2003/0149476 A1 | 8/2003 | Damm et al. | |
| 2003/0149478 A1 | 8/2003 | Figulla et al. | |
| 2003/0153974 A1 | 8/2003 | Spenser et al. | |
| 2003/0181850 A1 | 9/2003 | Diamond et al. | |
| 2003/0191519 A1 | 10/2003 | Lombardi et al. | |
| 2003/0199913 A1 | 10/2003 | Dubrul | |
| 2003/0199963 A1 | 10/2003 | Tower et al. | |
| 2003/0199971 A1 | 10/2003 | Tower et al. | |
| 2003/0212410 A1 | 11/2003 | Stenzel et al. | |
| 2003/0212454 A1 | 11/2003 | Scott et al. | |
| 2003/0225445 A1 | 12/2003 | Derus et al. | |
| 2003/0233140 A1 * | 12/2003 | Hartley et al. | 623/1.11 |
| 2004/0019374 A1 | 1/2004 | Hojeibane et al. | |
| 2004/0034411 A1 | 2/2004 | Quijano et al. | |
| 2004/0039436 A1 | 2/2004 | Spenser et al. | |
| 2004/0049224 A1 | 3/2004 | Buehlmann et al. | |
| 2004/0049262 A1 | 3/2004 | Obermiller et al. | |
| 2004/0049266 A1 | 3/2004 | Anduiza et al. | |
| 2004/0059413 A1 * | 3/2004 | Argento | 623/2.11 |
| 2004/0082904 A1 | 4/2004 | Houde et al. | |
| 2004/0088045 A1 | 5/2004 | Cox | |
| 2004/0092858 A1 | 5/2004 | Wilson et al. | |
| 2004/0092989 A1 | 5/2004 | Wilson et al. | |
| 2004/0093005 A1 | 5/2004 | Durcan | |
| 2004/0093060 A1 | 5/2004 | Seguin et al. | |
| 2004/0093075 A1 | 5/2004 | Kuehne | |
| 2004/0097788 A1 | 5/2004 | Mourlas et al. | |
| 2004/0098112 A1 | 5/2004 | DiMatteo et al. | |
| 2004/0106976 A1 | 6/2004 | Bailey et al. | |
| 2004/0106990 A1 | 6/2004 | Spence et al. | |
| 2004/0111096 A1 | 6/2004 | Tu et al. | |
| 2004/0116951 A1 | 6/2004 | Rosengart | |
| 2004/0117004 A1 | 6/2004 | Osborne et al. | |
| 2004/0122468 A1 | 6/2004 | Yodfat et al. | |
| 2004/0122514 A1 | 6/2004 | Fogarty et al. | |
| 2004/0122516 A1 | 6/2004 | Fogarty | |
| 2004/0127979 A1 | 7/2004 | Wilson | |
| 2004/0138742 A1 | 7/2004 | Myers et al. | |
| 2004/0138743 A1 | 7/2004 | Myers et al. | |
| 2004/0153146 A1 | 8/2004 | Lashinski et al. | |
| 2004/0167573 A1 | 8/2004 | Williamson | |
| 2004/0167620 A1 | 8/2004 | Ortiz | |
| 2004/0186514 A1 | 9/2004 | Swain et al. | |
| 2004/0186563 A1 | 9/2004 | Lobbi | |
| 2004/0193261 A1 | 9/2004 | Berreklouw | |
| 2004/0210240 A1 | 10/2004 | Saint | |
| 2004/0210304 A1 | 10/2004 | Seguin et al. | |
| 2004/0210307 A1 | 10/2004 | Khairkhahan | |
| 2004/0215333 A1 | 10/2004 | Duran | |
| 2004/0215339 A1 | 10/2004 | Drasler et al. | |
| 2004/0220655 A1 * | 11/2004 | Swanson et al. | 623/1.11 |
| 2004/0225353 A1 | 11/2004 | McGuckin, Jr. | |
| 2004/0225354 A1 | 11/2004 | Allen | |
| 2004/0254636 A1 | 12/2004 | Flagle et al. | |
| 2004/0260383 A1 | 12/2004 | Stelter et al. | |
| 2004/0260389 A1 | 12/2004 | Case et al. | |
| 2004/0260394 A1 | 12/2004 | Douk et al. | |
| 2004/0267357 A1 | 12/2004 | Allen et al. | |
| 2005/0010246 A1 | 1/2005 | Streeter | |

(56) References Cited

U.S. PATENT DOCUMENTS

| | | |
|---|---|---|
| 2005/0010285 A1 | 1/2005 | Lambrecht et al. |
| 2005/0010287 A1 | 1/2005 | Macoviak |
| 2005/0015112 A1 | 1/2005 | Cohn et al. |
| 2005/0027348 A1 | 2/2005 | Case et al. |
| 2005/0033398 A1 | 2/2005 | Seguin |
| 2005/0043790 A1 | 2/2005 | Seguin |
| 2005/0049692 A1 | 3/2005 | Numamoto |
| 2005/0049696 A1 | 3/2005 | Siess |
| 2005/0055088 A1 | 3/2005 | Liddicoat et al. |
| 2005/0060029 A1 | 3/2005 | Le |
| 2005/0060030 A1 | 3/2005 | Lashinski et al. |
| 2005/0075584 A1 | 4/2005 | Cali |
| 2005/0075712 A1 | 4/2005 | Biancucci |
| 2005/0075717 A1 | 4/2005 | Nguyen |
| 2005/0075719 A1 | 4/2005 | Bergheim |
| 2005/0075724 A1 | 4/2005 | Svanidze |
| 2005/0075727 A1 | 4/2005 | Wheatley |
| 2005/0075730 A1 | 4/2005 | Myers |
| 2005/0075731 A1 | 4/2005 | Artof |
| 2005/0085841 A1 | 4/2005 | Eversull et al. |
| 2005/0085842 A1 | 4/2005 | Eversull et al. |
| 2005/0085843 A1 | 4/2005 | Opolski et al. |
| 2005/0085890 A1 | 4/2005 | Rasmussen et al. |
| 2005/0085900 A1 | 4/2005 | Case et al. |
| 2005/0096568 A1 | 5/2005 | Kato |
| 2005/0096692 A1 | 5/2005 | Linder et al. |
| 2005/0096724 A1 | 5/2005 | Stenzel et al. |
| 2005/0096734 A1 | 5/2005 | Majercak et al. |
| 2005/0096735 A1 | 5/2005 | Hojeibane et al. |
| 2005/0096736 A1 | 5/2005 | Osse et al. |
| 2005/0096738 A1 | 5/2005 | Cali et al. |
| 2005/0107871 A1 | 5/2005 | Realyvasquez et al. |
| 2005/0113910 A1 | 5/2005 | Paniagua |
| 2005/0119688 A1 | 6/2005 | Bergheim |
| 2005/0119719 A1* | 6/2005 | Wallace et al. .............. 623/1.11 |
| 2005/0131438 A1 | 6/2005 | Cohn |
| 2005/0137686 A1 | 6/2005 | Salahieh |
| 2005/0137688 A1 | 6/2005 | Salahieh et al. |
| 2005/0137692 A1 | 6/2005 | Haug |
| 2005/0137695 A1 | 6/2005 | Salahieh |
| 2005/0137701 A1 | 6/2005 | Salahieh |
| 2005/0143807 A1 | 6/2005 | Pavcnik et al. |
| 2005/0143809 A1 | 6/2005 | Salahieh |
| 2005/0148997 A1 | 7/2005 | Valley et al. |
| 2005/0149181 A1 | 7/2005 | Eberhardt |
| 2005/0165477 A1 | 7/2005 | Anduiza et al. |
| 2005/0187616 A1 | 8/2005 | Realyvasquez |
| 2005/0197695 A1 | 9/2005 | Stacchino et al. |
| 2005/0203549 A1 | 9/2005 | Realyvasquez |
| 2005/0203605 A1 | 9/2005 | Dolan |
| 2005/0203618 A1 | 9/2005 | Sharkawy |
| 2005/0222674 A1 | 10/2005 | Paine |
| 2005/0228495 A1 | 10/2005 | Macoviak |
| 2005/0234546 A1 | 10/2005 | Nugent |
| 2005/0240200 A1 | 10/2005 | Bergheim |
| 2005/0240263 A1 | 10/2005 | Fogarty et al. |
| 2005/0261759 A1 | 11/2005 | Lambrecht et al. |
| 2005/0283962 A1 | 12/2005 | Boudjemline |
| 2005/0288764 A1 | 12/2005 | Snow et al. |
| 2006/0004439 A1 | 1/2006 | Spenser et al. |
| 2006/0004469 A1 | 1/2006 | Sokel |
| 2006/0009841 A1 | 1/2006 | McGuckin et al. |
| 2006/0052867 A1 | 3/2006 | Revuelta et al. |
| 2006/0058775 A1 | 3/2006 | Stevens et al. |
| 2006/0089711 A1 | 4/2006 | Dolan |
| 2006/0095119 A1 | 5/2006 | Bolduc |
| 2006/0100685 A1 | 5/2006 | Seguin et al. |
| 2006/0100686 A1* | 5/2006 | Bolduc et al. ................ 623/1.11 |
| 2006/0111771 A1 | 5/2006 | Ton et al. |
| 2006/0116757 A1 | 6/2006 | Lashinski et al. |
| 2006/0135964 A1 | 6/2006 | Vesely |
| 2006/0142848 A1 | 6/2006 | Gabbay |
| 2006/0161249 A1* | 7/2006 | Realyvasquez et al. ...... 623/2.11 |
| 2006/0167474 A1 | 7/2006 | Bloom et al. |
| 2006/0173524 A1* | 8/2006 | Salahieh et al. .............. 623/1.11 |
| 2006/0178740 A1 | 8/2006 | Stacchino et al. |
| 2006/0195134 A1 | 8/2006 | Crittenden |
| 2006/0206192 A1 | 9/2006 | Tower et al. |
| 2006/0206202 A1 | 9/2006 | Bonhoefer et al. |
| 2006/0212111 A1 | 9/2006 | Case et al. |
| 2006/0247763 A1 | 11/2006 | Slater |
| 2006/0259134 A1 | 11/2006 | Schwammenthal et al. |
| 2006/0259136 A1 | 11/2006 | Nguyen et al. |
| 2006/0259137 A1 | 11/2006 | Artof et al. |
| 2006/0265056 A1 | 11/2006 | Nguyen et al. |
| 2006/0271097 A1 | 11/2006 | Ramzipoor et al. |
| 2006/0271166 A1 | 11/2006 | Thill et al. |
| 2006/0271175 A1 | 11/2006 | Woolfson et al. |
| 2006/0276874 A1 | 12/2006 | Wilson et al. |
| 2006/0276882 A1 | 12/2006 | Case et al. |
| 2006/0282150 A1* | 12/2006 | Olson et al. .................. 623/1.11 |
| 2006/0282161 A1 | 12/2006 | Huynh et al. |
| 2007/0005129 A1 | 1/2007 | Damm et al. |
| 2007/0005131 A1 | 1/2007 | Taylor |
| 2007/0010878 A1 | 1/2007 | Rafiee et al. |
| 2007/0016286 A1 | 1/2007 | Herrmann et al. |
| 2007/0027518 A1 | 2/2007 | Case et al. |
| 2007/0027533 A1 | 2/2007 | Douk |
| 2007/0038295 A1 | 2/2007 | Case et al. |
| 2007/0043431 A1 | 2/2007 | Melsheimer |
| 2007/0043435 A1 | 2/2007 | Seguin et al. |
| 2007/0051377 A1 | 3/2007 | Douk et al. |
| 2007/0055340 A1* | 3/2007 | Pryor ........................... 623/1.11 |
| 2007/0061008 A1* | 3/2007 | Salahieh et al. .............. 623/2.11 |
| 2007/0073389 A1* | 3/2007 | Bolduc et al. ................ 623/1.36 |
| 2007/0073392 A1 | 3/2007 | Heyninck-Jantz |
| 2007/0078509 A1 | 4/2007 | Lotfy et al. |
| 2007/0078510 A1 | 4/2007 | Ryan |
| 2007/0088431 A1 | 4/2007 | Bourang et al. |
| 2007/0093869 A1 | 4/2007 | Bloom et al. |
| 2007/0100419 A1 | 5/2007 | Licata et al. |
| 2007/0100439 A1 | 5/2007 | Cangialosi |
| 2007/0100440 A1 | 5/2007 | Figulla |
| 2007/0100449 A1 | 5/2007 | O'Neil et al. |
| 2007/0112355 A1* | 5/2007 | Salahieh et al. .............. 606/108 |
| 2007/0112415 A1 | 5/2007 | Bartlett |
| 2007/0112422 A1 | 5/2007 | Dehdashtian |
| 2007/0162102 A1 | 7/2007 | Ryan et al. |
| 2007/0162113 A1 | 7/2007 | Sharkawy et al. |
| 2007/0185513 A1 | 8/2007 | Woolfson et al. |
| 2007/0203391 A1 | 8/2007 | Bloom et al. |
| 2007/0225681 A1 | 9/2007 | House |
| 2007/0232898 A1 | 10/2007 | Huynh et al. |
| 2007/0233228 A1 | 10/2007 | Eberhardt et al. |
| 2007/0233237 A1 | 10/2007 | Krivoruchko |
| 2007/0233238 A1 | 10/2007 | Huynh et al. |
| 2007/0238979 A1 | 10/2007 | Huynh et al. |
| 2007/0239254 A1 | 10/2007 | Marchand et al. |
| 2007/0239265 A1 | 10/2007 | Birdsall |
| 2007/0239266 A1 | 10/2007 | Birdsall |
| 2007/0239269 A1 | 10/2007 | Dolan et al. |
| 2007/0239271 A1 | 10/2007 | Nguyen |
| 2007/0239273 A1 | 10/2007 | Allen |
| 2007/0244544 A1 | 10/2007 | Birdsall et al. |
| 2007/0244545 A1 | 10/2007 | Birdsall et al. |
| 2007/0244546 A1 | 10/2007 | Francis |
| 2007/0244553 A1 | 10/2007 | Rafiee et al. |
| 2007/0244554 A1 | 10/2007 | Rafiee et al. |
| 2007/0244555 A1 | 10/2007 | Rafiee et al. |
| 2007/0244556 A1 | 10/2007 | Rafiee et al. |
| 2007/0244557 A1 | 10/2007 | Rafiee et al. |
| 2007/0250160 A1 | 10/2007 | Rafiee |
| 2007/0255394 A1 | 11/2007 | Ryan |
| 2007/0255396 A1 | 11/2007 | Douk et al. |
| 2007/0288000 A1 | 12/2007 | Bonan |
| 2008/0004696 A1 | 1/2008 | Vesely |
| 2008/0009940 A1 | 1/2008 | Cribier |
| 2008/0015671 A1 | 1/2008 | Bonhoeffer |
| 2008/0021552 A1 | 1/2008 | Gabbay |
| 2008/0027529 A1 | 1/2008 | Hartley et al. |
| 2008/0048656 A1 | 2/2008 | Tan |
| 2008/0065011 A1 | 3/2008 | Marchand et al. |
| 2008/0065206 A1 | 3/2008 | Liddicoat |
| 2008/0071361 A1 | 3/2008 | Tuval et al. |

(56) References Cited

U.S. PATENT DOCUMENTS

| | | |
|---|---|---|
| 2008/0071362 A1 | 3/2008 | Tuval et al. |
| 2008/0071363 A1 | 3/2008 | Tuval et al. |
| 2008/0071366 A1 | 3/2008 | Tuval et al. |
| 2008/0071368 A1 | 3/2008 | Tuval et al. |
| 2008/0077234 A1 | 3/2008 | Styrc |
| 2008/0082159 A1 | 4/2008 | Tseng et al. |
| 2008/0082165 A1 | 4/2008 | Wilson et al. |
| 2008/0082166 A1 | 4/2008 | Styrc et al. |
| 2008/0133003 A1 | 6/2008 | Seguin et al. |
| 2008/0140189 A1 | 6/2008 | Nguyen et al. |
| 2008/0147105 A1 | 6/2008 | Wilson et al. |
| 2008/0147180 A1 | 6/2008 | Ghione et al. |
| 2008/0147181 A1 | 6/2008 | Ghione et al. |
| 2008/0147182 A1 | 6/2008 | Righini et al. |
| 2008/0154355 A1 | 6/2008 | Benichow et al. |
| 2008/0154356 A1 | 6/2008 | Obermiller et al. |
| 2008/0161910 A1 | 7/2008 | Revuelta et al. |
| 2008/0161911 A1 | 7/2008 | Revuelta et al. |
| 2008/0183273 A1 | 7/2008 | Mesana et al. |
| 2008/0188869 A1* | 8/2008 | Weitzner et al. ............ 606/130 |
| 2008/0188928 A1 | 8/2008 | Salahieh et al. |
| 2008/0215143 A1 | 9/2008 | Seguin et al. |
| 2008/0215144 A1 | 9/2008 | Ryan et al. |
| 2008/0221666 A1 | 9/2008 | Licata et al. |
| 2008/0228254 A1 | 9/2008 | Ryan |
| 2008/0228263 A1 | 9/2008 | Ryan |
| 2008/0234797 A1 | 9/2008 | Styrc |
| 2008/0243246 A1 | 10/2008 | Ryan et al. |
| 2008/0255651 A1 | 10/2008 | Dwork |
| 2008/0255660 A1 | 10/2008 | Guyenot et al. |
| 2008/0255661 A1 | 10/2008 | Straubinger et al. |
| 2008/0262593 A1 | 10/2008 | Ryan et al. |
| 2008/0269878 A1 | 10/2008 | Iobbi |
| 2009/0005863 A1 | 1/2009 | Goetz et al. |
| 2009/0012600 A1 | 1/2009 | Styrc et al. |
| 2009/0048656 A1* | 2/2009 | Wen ............... 623/1.12 |
| 2009/0054976 A1 | 2/2009 | Tuval et al. |
| 2009/0069886 A1 | 3/2009 | Suri et al. |
| 2009/0069887 A1 | 3/2009 | Righini et al. |
| 2009/0069889 A1 | 3/2009 | Suri et al. |
| 2009/0082858 A1 | 3/2009 | Nugent et al. |
| 2009/0085900 A1 | 4/2009 | Weiner |
| 2009/0099653 A1 | 4/2009 | Suri et al. |
| 2009/0138072 A1* | 5/2009 | Gendreau ............ 623/1.15 |
| 2009/0138079 A1 | 5/2009 | Tuval et al. |
| 2009/0164004 A1 | 6/2009 | Cohn |
| 2009/0164006 A1 | 6/2009 | Seguin et al. |
| 2009/0171447 A1 | 7/2009 | VonSegesser et al. |
| 2009/0192585 A1 | 7/2009 | Bloom et al. |
| 2009/0192586 A1 | 7/2009 | Tabor et al. |
| 2009/0192591 A1 | 7/2009 | Ryan et al. |
| 2009/0198316 A1 | 8/2009 | Laske et al. |
| 2009/0216310 A1 | 8/2009 | Straubinger et al. |
| 2009/0216312 A1 | 8/2009 | Straubinger et al. |
| 2009/0216313 A1 | 8/2009 | Straubinger et al. |
| 2009/0222082 A1 | 9/2009 | Lock et al. |
| 2009/0234443 A1 | 9/2009 | Ottma et al. |
| 2009/0240264 A1 | 9/2009 | Tuval et al. |
| 2009/0240320 A1 | 9/2009 | Tuval |
| 2009/0287296 A1 | 11/2009 | Manasse |
| 2010/0004740 A1 | 1/2010 | Seguin et al. |
| 2010/0030328 A1 | 2/2010 | Seguin et al. |
| 2010/0036479 A1 | 2/2010 | Hill et al. |
| 2010/0036485 A1 | 2/2010 | Seguin |
| 2010/0069852 A1 | 3/2010 | Kelley |
| 2010/0094411 A1 | 4/2010 | Tuval et al. |
| 2010/0100167 A1 | 4/2010 | Bortlein et al. |
| 2010/0131054 A1 | 5/2010 | Tuval et al. |
| 2010/0137979 A1 | 6/2010 | Tuval et al. |
| 2010/0145439 A1 | 6/2010 | Seguin et al. |
| 2010/0152840 A1 | 6/2010 | Seguin et al. |
| 2010/0161045 A1 | 6/2010 | Righini |
| 2010/0198346 A1 | 8/2010 | Keogh et al. |
| 2010/0234940 A1 | 9/2010 | Dolan |
| 2010/0256723 A1 | 10/2010 | Murray |

FOREIGN PATENT DOCUMENTS

| | | |
|---|---|---|
| DE | 195 32 846 | 3/1997 |
| DE | 195 46 692 A1 | 6/1997 |
| DE | 195 46 692 C2 | 6/1997 |
| DE | 198 57 887 A1 | 7/2000 |
| DE | 199 07 646 | 8/2000 |
| DE | 100 10 074 | 10/2001 |
| DE | 100 49 812 | 4/2002 |
| DE | 100 49 813 | 4/2002 |
| DE | 100 49 815 | 4/2002 |
| EP | 0829242 A1 | 3/1998 |
| EP | 1057460 A1 | 6/2000 |
| EP | 1255510 | 11/2002 |
| EP | 1469797 | 11/2005 |
| EP | 1719452 A1 | 11/2006 |
| FR | 2788217 | 12/1999 |
| FR | 2815844 | 5/2000 |
| GB | 2056023 | 3/1981 |
| GB | 2433700 | 12/2007 |
| SU | 1271508 | 11/1986 |
| WO | 95/29640 | 11/1995 |
| WO | 00/44313 | 8/2000 |
| WO | 00/47136 | 8/2000 |
| WO | 01/35870 | 5/2001 |
| WO | 01/49213 | 7/2001 |
| WO | 01/54625 | 8/2001 |
| WO | 01/62189 | 8/2001 |
| WO | 01/64137 | 9/2001 |
| WO | 02/22054 | 3/2002 |
| WO | 02/36048 | 5/2002 |
| WO | 03/003943 | 1/2003 |
| WO | 03/003949 | 1/2003 |
| WO | 03/011195 | 2/2003 |
| WO | 2004/019825 | 3/2004 |
| WO | 2004/089250 | 10/2004 |
| WO | 2005/004753 | 1/2005 |
| WO | 2005/046528 | 5/2005 |
| WO | 2006/026371 | 3/2006 |
| WO | 2008/047354 | 4/2008 |
| WO | 2008/138584 | 11/2008 |
| WO | 2008/150529 | 12/2008 |
| WO | 2009/002548 | 12/2008 |
| WO | 2009/029199 | 3/2009 |
| WO | 2009/042196 | 4/2009 |
| WO | 2009/045338 | 4/2009 |
| WO | WO 2009/042196 A2 | 4/2009 |
| WO | 2009/061389 | 5/2009 |
| WO | 2009/091509 | 7/2009 |
| WO | 2009/111241 | 9/2009 |

OTHER PUBLICATIONS

Babaliaros, et al., "State of the Art Percutaneous Intervention for the Treatment of Valvular Heart Disease: A Review of the Current Technologies and Ongoing Research in the Field of Percutaneous Heart Valve Replacement and Repair," Cardiology 2007; 107:87-96.

Bailey, "Percutaneous Expandable Prosthetic Valves," In: Topol EJ, ed. Textbook of Interventional Cardiology. Volume II. Second edition. WB Saunders, Philadelphia, 1994:1268-1276.

Block, et al., "Percutaneous Approaches to Valvular Heart Disease," Current Cardiology Reports, vol. 7 (2005) pp. 108-113.

Bonhoeffer, et al., "Percutaneous Insertion of the Pulmonary Valve," Journal of the American College of Cardiology (United States), May 15, 2002, pp. 1664-1669.

Bonhoeffer, et al, "Percutaneous Replacement of Pulmonary Valve in a Right-Ventricle to Pulmonary-Artery Prosthetic Conduit with Valve Dysfunction," Lancet (England), Oct. 21, 2000, pp. 1403-1405.

Bonhoeffer, et al., "Transcatheter Implantation of a Bovine Valve in Pulmonary Position: A Lamb Study," Circulation (United States), Aug. 15, 2000, pp. 813-816.

Boudjemline, et al, "Images in Cardiovascular Medicine. Percutaneous Aortic Valve Replacement in Animals," Circulation (United States), Mar. 16, 2004, 109, p. e161.

Boudjemline, et al, "Is Percutaneous Implantation of a Bovine Venous Valve in the Inferior Vena Cava a Reliable Technique to Treat Chronic Venous Insufficiency Syndrome?" Medical Science Moni-

(56) References Cited

OTHER PUBLICATIONS tor—International Medical Journal of Experimental and Clinical Research (Poland), Mar. 2004, pp. BR61-BR66.
Boudjemline, et al, "Off-pump Replacement of the Pulmonary Valve in Large Right Ventricular Outflow Tracts: A Hybrid Approach," Journal of Thoracic and Cardiovascular Surgery (United States), Apr. 2005, pp. 831-837.
Boudjemline, et al, "Percutaneous Aortic Valve Replacement: Will We Get There?" Heart (British Cardiac Society) (England), Dec. 2001, pp. 705-706.
Boudjemline, et al, "Percutaneous Implantation of a Biological Valve in the Aorta to Treat Aortic Valve Insufficiency—A Sheep Study," Medical Science Monitor—International Medical Journal of Experimental and Clinical Research (Poland), Apr. 2002, pp. BR113-BR116.
Boudjemline, et al, "Percutaneous Implantation of a Biological Valve in Aortic Position: Preliminary Results in a Sheep Study," European Heart Journal 22, Sep. 2001, p. 630.
Boudjemline, et al, "Percutaneous Implantation of a Valve in the Descending Aorta in Lambs," European Heart Journal (England), Jul. 2002, pp. 1045-1049.
Boudjemline, et al, "Percutaneous Pulmonary Valve Replacement in a Large Right Ventricular Outflow Tract: An Experimental Study," Journal of the American College of Cardiology (United States), Mar. 17, 2004, pp. 1082-1087.
Boudjemline, et al, "Percutaneous Valve Insertion: A New Approach," Journal of Thoracic and Cardiovascular Surgery (United States), Mar. 2003, pp. 741-742.
Boudjemline, et al, "Stent Implantation Combined with a Valve Replacement to Treat Degenerated Right Ventricle to Pulmonary Artery Prosthetic Conduits," European Heart Journal 22, Sep. 2001, p. 355.
Boudjemline, et al, "Steps Toward Percutaneous Aortic Valve Replacement," Circulation (United States), Feb. 12, 2002, pp. 775-778.
Boudjemline, et al, "The Percutaneous Implantable Heart Valve," Progress in Pediatric Cardiology (Ireland), 2001, pp. 89-93.
Boudjemline, et al, "Transcatheter Reconstruction of the Right Heart," Cardiology in the Young (England), Jun. 2003, pp. 308-311.
Coats, et al, "The Potential Impact of Percutaneous Pulmonary Valve Stent Implantation on Right Ventricular Outflow Tract Re-Intervention," European Journal of Cardio-Thoracic Surgery (England), Apr. 2005, pp. 536-543.
Cribier, A. et al, "Percutaneous Transcatheter Implantation of an Aortic Valve Prosthesis for Calcific Aortic Stenosis: First Human Case Description," Circulation (2002) 3006-3008.
Davidson et al., "Percutaneous therapies for valvular heart disease," Cardiovascular Pathology 15 (2006) 123-129.
Hanzel, et al., "Complications of percutaneous aortic valve replacement: experience with the Criber-Edwards™ percutaneous heart valve," EuroIntervention Supplements (2006), 1 (Supplement A) A3-A8.
Huber, et al., "Do Valved Stents Compromise Coronary Flow?" Eur. J. Cardiothorac. Surg. 2004;25:754-759.
Khambadkone, "Nonsurgical Pulmonary Valve Replacement: Why, When, and How?" Catheterization and Cardiovascular Interventions—Official Journal of the Society for Cardiac Angiography & Interventions (United States), Jul. 2004, pp. 401-408.
Khambadkone, et al, "Percutaneous Implantation of Pulmonary Valves," Expert Review of Cardiovascular Therapy (England), Nov. 2003, pp. 541-548.
Khambadkone, et al, "Percutaneous Pulmonary Valve Implantation: Early and Medium Term Results," Circulation 108 (17 Supplement), Oct. 28, 2003, p. IV-375.
Khambadkone, et al, "Percutaneous Pulmonary Valve Implantation: Impact of Morphology on Case Selection," Circulation 108 (17 Supplement), Oct. 28, 2003, p. IV-642-IV-643.
Lutter, et al, "Percutaneous Aortic Valve Replacement: An Experimental Study. I. Studies on Implantation," The Journal of Thoracic and Cardiovascular Surgery, Apr. 2002, pp. 768-776.
Lutter, et al, "Percutaneous Valve Replacement: Current State and Future Prospects," Annals of Thoracic Surgery (Netherlands), Dec. 2004, pp. 2199-2206.
Ma, Ling, et al.., "Double-crowned valved stents for off-pump mitral valve replacement," European Journal of Cardio Thoracic Surgery, 28:194-198, 2005.
Medtech Insight, "New Frontiers in Heart Valve Disease," vol. 7, No. 8 (2005).
Palacios, "Percutaneous Valve Replacement and Repair, Fiction or Reality?" Journal of American College of Cardiology, vol. 44, No. 8 (2004) pp. 1662-1663.
Pelton et al., "Medical Uses of Nitinol," Materials Science Forum vols. 327-328, pp. 63-70 (2000).
Ruiz, "Transcathether Aortic Valve Implantation and Mitral Valve Repair: State of the Art," Pediatric Cardiology, vol. 26, No. 3 (2005).
Saliba, et al, "Treatment of Obstructions of Prosthetic Conduits by Percutaneous Implantation of Stents," Archives des Maldies du Coeur et des Vaisseaux (France), 1999, pp. 591-596.
Webb, et al., "Percutaneous Aortic Valve Implantation Retrograde from the Femoral Artery," Circulation (2006), 113;842-850.
Stassano et al., "Mid-term results of the valve-on-valve technique for bioprosthetic failure," Eur. J. Cardiothorac. Surg. 2000; 18:453-457.
Pavcnik et al., "Aortic and venous valve for percutaneous insertion," Min. Invas. Ther. & Allied Techol. 2000, vol. 9, pp. 287-292.
European Patent Office Communication in Application No. 09 704 087.7-2320, Dated Nov. 30, 2012, 5 pages.

\* cited by examiner

DELIVERY SYSTEMS AND METHODS OF IMPLANTATION FOR PROSTHETIC HEART VALVES

CROSS-REFERENCE TO RELATED APPLICATION

The present application is a continuation of U.S. application Ser. No. 12/357,980, filed Jan. 22, 2009 now U.S. Pat. No. 8,157,853, which claims priority to U.S. Provisional Application No. 61/062,207, filed Jan. 24, 2008, and titled "Delivery Systems and Methods of Implantation for Prosthetic Heart Valves", the contents of which are incorporated herein by reference in its entirety.

TECHNICAL FIELD

The present invention relates to prosthetic heart valves. More particularly, it relates to devices, methods, and delivery systems for percutaneously implanting prosthetic heart valves.

BACKGROUND

Diseased or otherwise deficient heart valves can be repaired or replaced using a variety of different types of heart valve surgeries. Typical heart valve surgeries involve an open-heart surgical procedure that is conducted under general anesthesia, during which the heart is stopped while blood flow is controlled by a heart-lung bypass machine. This type of valve surgery is highly invasive and exposes the patient to a number of potentially serious risks, such as infection, stroke, renal failure, and adverse effects associated with use of the heart-lung machine, for example.

Recently, there has been increasing interest in minimally invasive and percutaneous replacement of cardiac valves. Such surgical techniques involve making a very small opening in the skin of the patient into which a valve assembly is inserted in the body and delivered to the heart via a delivery device similar to a catheter. This technique is often preferable to more invasive forms of surgery, such as the open-heart surgical procedure described above. In the context of pulmonary valve replacement, U.S. Patent Application Publication Nos. 2003/0199971 A1 and 2003/0199963 A1, both filed by Tower, et al., describe a valved segment of bovine jugular vein, mounted within an expandable stent, for use as a replacement pulmonary valve. The replacement valve is mounted on a balloon catheter and delivered percutaneously via the vascular system to the location of the failed pulmonary valve and expanded by the balloon to compress the valve leaflets against the right ventricular outflow tract, anchoring and sealing the replacement valve. As described in the articles: "Percutaneous Insertion of the Pulmonary Valve", Bonhoeffer, et al., Journal of the American College of Cardiology 2002; 39: 1664-1669 and "Transcatheter Replacement of a Bovine Valve in Pulmonary Position", Bonhoeffer, et al., Circulation 2000; 102: 813-816, the replacement pulmonary valve may be implanted to replace native pulmonary valves or prosthetic pulmonary valves located in valved conduits.

Various types and configurations of prosthetic heart valves are used in percutaneous valve procedures to replace diseased natural human heart valves. The actual shape and configuration of any particular prosthetic heart valve is dependent to some extent upon the valve being replaced (i.e., mitral valve, tricuspid valve, aortic valve, or pulmonary valve). In general, the prosthetic heart valve designs attempt to replicate the function of the valve being replaced and thus will include valve leaflet-like structures used with either bioprostheses or mechanical heart valve prostheses. In other words, the replacement valves may include a valved vein segment that is mounted in some manner within an expandable stent to make a stented valve. In order to prepare such a valve for percutaneous implantation, the stented valve can be initially provided in an expanded or uncrimped condition, then crimped or compressed around the balloon portion of a catheter until it is as close to the diameter of the catheter as possible.

Other percutaneously delivered prosthetic heart valves have been suggested having a generally similar configuration, such as by Bonhoeffer, P. et al., "Transcatheter Implantation of a Bovine Valve in Pulmonary Position." Circulation, 2002; 102:813-816, and by Cribier, A. et al. "Percutaneous Transcatheter Implantation of an Aortic Valve Prosthesis for Calcific Aortic Stenosis." Circulation, 2002; 106:3006-3008, the disclosures of which are incorporated herein by reference. These techniques rely at least partially upon a frictional type of engagement between the expanded support structure and the native tissue to maintain a position of the delivered prosthesis, although the stents can also become at least partially embedded in the surrounding tissue in response to the radial force provided by the stent and balloons that are sometimes used to expand the stent. Thus, with these transcatheter techniques, conventional sewing of the prosthetic heart, valve to the patient's native tissue is not necessary. Similarly, in an article by Bonhoeffer, P. et al. titled "Percutaneous Insertion of the Pulmonary Valve." J Am Coll Cardiol, 2002; 39:1664-1669, the disclosure of which is incorporated herein by reference, percutaneous delivery of a biological valve is described. The valve is sutured to an expandable stent within a previously implanted valved or non-valved conduit, or a previously implanted valve. Again, radial expansion of the secondary valve stent is used for placing and maintaining the replacement valve.

Some delivery systems used for percutaneous delivery of heart valves have had associated issues with the heart valves sticking or otherwise not consistently releasing from the delivery system for deployment into the desired location in the patient. In these cases, the delivery system can be further manipulated, which may cause the valve to become dislodged from the desired implantation location or cause other trauma to the patient. In rare cases, the heart valve cannot be released from the delivery system, which can then require emergency surgery to intervene. Such surgery can expose the patient to significant risk and trauma.

Although there have been advances in percutaneous valve replacement techniques and devices, there is a continued desire to provide different designs of cardiac valves that can be implanted in a minimally invasive and percutaneous manner. There is also a continued desire to be able to reposition and/or retract the valves once they have been deployed or partially deployed in order to ensure optimal placement of the valves within the patient. In particular, it would be advantageous to provide a valve and corresponding delivery system that allow for full or partial repositionability and/or retractability of the valve once it is positioned in the patient. In addition, it would be advantageous to provide a delivery system that can consistently release a heart valve without inducing the application of force to the stented valve that can dislodge the valve from the desired implantation location. Finally, the complexity and widely varying geometries associated with transcatheter valved stents and the complex anatomies that they are designed to accommodate present a need to be able to sequentially release specific regions or portions of the transcatheter valved stent. This enables specific advantages to position the devices more accurately and/or deploy specific features for anchoring, sealing, or docking of the devices. Additionally, the ability to sequence the release of various regions of different radial force and/or geometry is important in improving deliverability of transcatheter valve devices.

SUMMARY

Replacement heart valves that can be used with delivery systems of the invention each include a stent within which a valve structure can be attached. The stents used with delivery systems and methods of the invention include a wide variety of structures and features that can be used alone or in combination with other stent features. In particular, these stents provide a number of different docking and/or anchoring structures that are conducive to percutaneous delivery thereof. Many of the stent structures are thus compressible to a relatively small diameter for percutaneous delivery to the heart of the patient, and then are expandable either via removal of external compressive forces (e.g., self-expanding stents), or through application of an outward radial force (e.g., balloon expandable stents). The devices delivered by the delivery systems described herein can be used to deliver stents, valved stents, or other interventional devices such as ASD (atrial septal defect) closure devices, VSD (ventricular septal defect) closure devices, or PFO (patent foramen ovale) occluders.

Methods for insertion of the replacement heart valves of the invention include delivery systems that can maintain the stent structures in their compressed state during their insertion and allow or cause the stent structures to expand once they are in their desired location. In particular, the methods of implanting a stent can include the use of delivery systems or a valved stent having a plurality of wires with coiled or pigtail ends attached to features of the stent frame. The coiled wire ends can be straightened or uncoiled to release the stent to which they are attached. The coiled or pigtail wire end configuration allows for positive, consistent release of the stent from the delivery system without the associated complications that can be caused by incomplete release and/or sticking that can occur with other delivery systems. In addition, the release of a stent from a delivery system having coiled wire ends does not require the direct application of force to the stented valve that can dislodge the valve from the desired implantation location.

Delivery systems and methods of the invention can include features that allow the stents to be retrieved for removal or relocation thereof after they have been deployed or partially deployed from the stent delivery systems. The methods may include implantation of the stent structures using either an antegrade or retrograde approach. Further, in many of the delivery approaches of the invention, the stent structure is rotatable in vivo to allow the stent structure to be positioned in a desired orientation.

Delivery systems and methods of the invention provide for sequential release of portions of the heart valve. That is, the delivery system has actuation capabilities for disengaging from one or more structural features of a heart valve in a first step, then disengaging from additional structural features of that heart valve in one or more sequential steps. In this way, the deployment of the heart valve can be performed relatively gradually, which can provide the clinician with the opportunity to reposition or relocate the heart valve before it is completely released from the delivery system.

BRIEF DESCRIPTION OF THE DRAWINGS

The present invention will be further explained with reference to the appended Figures, wherein like structure is referred to by like numerals throughout the several views, and wherein.

DETAILED DESCRIPTION

Figure 1:
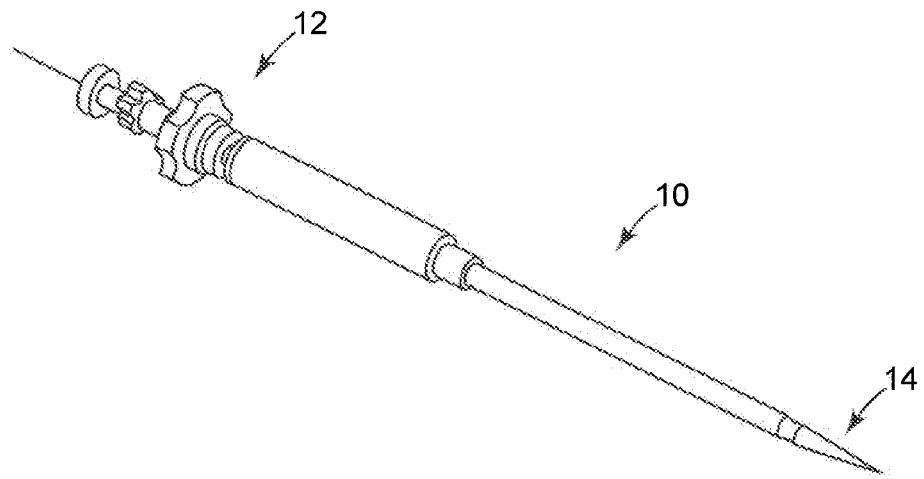
FIG. 1 is a perspective view of one embodiment of a delivery system of the invention.

As referred to herein, the prosthetic heart valves used in accordance with the various devices and methods of heart valve delivery may include a wide variety of different configurations, such as a prosthetic heart valve having tissue leaflets or a synthetic heart valve having polymeric, metallic, or tissue-engineered leaflets, and can be specifically configured for replacing any heart valve. That is, while much of the description herein refers to replacement of aortic valves, the prosthetic heart valves of the invention can also generally be used for replacement of native mitral, pulmonic, or tricuspid valves, for use as a venous valve, or to replace a failed bioprosthesis, such as in the area of an aortic valve or mitral valve, for example.

Each of the valves used with the delivery devices and methods described herein can include leaflets attached within an interior area of a stent; however, such leaflets are not shown in many of the illustrated embodiments for clarity purposes. In general, the stents used with the delivery systems and methods described herein include a support structure comprising a number of strut or wire portions arranged relative to each, other to provide a desired compressibility and strength to the heart valve. However, other stent structures can also be configured for use with delivery systems and methods of the invention, including stents that consist of foil or metal frames or inflatable lumens that can be filled with a hardenable material or agent, such as that proposed in U.S. Pat. No. 5,554,185 (Block), for example. Although a number of different configurations of stents can be used, in general terms, the stents described herein are generally tubular or cylindrical support structures, although the diameter and shape can vary along the length of the stent, and leaflets can be secured to the support structure to provide a valved stent. The leaflets can be formed from a variety of materials, such as autologous tissue, xenograph material, or synthetics as are known in the art. The leaflets may be provided as a homogenous, biological valve structure, such as a porcine, bovine, or equine valve. Alternatively, the leaflets can be provided independent of one another (e.g., bovine or equine pericardial leaflets) and subsequently assembled to the support structure of the stent. In another alternative, the stent and leaflets can be fabricated at the same time, such as may be accomplished using high strength nano-manufactured NiTi films of the type produced by Advanced Bio Prosthetic Surfaces Ltd. (ABPS) of San Antonio, Tex., for example. The support structures are generally configured to accommodate three leaflets; however, the prosthetic heart valves described herein can incorporate more or less than three leaflets.

In more general terms, the combination of a support structure with one or more leaflets can assume a variety of other configurations that differ from those shown and described, including any known prosthetic heart valve design. In certain embodiments of the invention, the support structure with leaflets can be any known expandable prosthetic heart valve configuration, whether balloon expandable, self-expanding, or unfurling (as described, for example, in U.S. Pat. Nos. 3,671,979; 4,056,854; 4,994,077; 5,332,402; 5,370,685; 5,397,351; 5,554,185; 5,855,601; and 6,168,614; U.S. Patent Application Publication No. 2004/0034411; Bonhoeffer P., et al., "Percutaneous Insertion of the Pulmonary Valve", Pediatric Cardiology, 2002; 39:1664-1669; Anderson H R, et al., "Transluminal Implantation of Artificial Heart Valves", EUR Heart J., 1992; 13:704-708; Anderson, J. R., et al., "Transluminal Catheter Implantation of New Expandable Artificial Cardiac Valve", EUR Heart J., 1990, 11: (Suppl) 224a; Hilbert S. L., "Evaluation of Explanted Polyurethane Trileaflet Cardiac Valve Prosthesis", J Thorac Cardiovascular Surgery, 1989; 94:419-29; Block P C, "Clinical and Hemodyamic Follow-Up After Percutaneous Aortic Valvuloplasty in the Elderly", The American Journal of Cardiology; Vol. 62, Oct. 1, 1998; Boudjemline, Y., "Steps Toward Percutaneous Aortic Valve Replacement", Circulation, 2002; 105:775-558; Bonhoeffer, P., "TranscatheterImplantation of a Bovine Valve in Pulmonary Position, a Lamb Study", Circulation, 2000:102: 813-816; Boudjemline, Y., "Percutaneous Implantation of a Valve in the Descending Aorta In Lambs", EUR Heart J, 2002; 23:1045-1049; Kulkinski, D., "Future Horizons in Surgical Aortic Valve Replacement: Lessons Learned During the Early Stages of Developing a Transluminal Implantation Technique", ASAIO J, 2004; 50:364-68; the teachings of which are all incorporated herein by reference).

Optional orientation and positioning of the stents of the invention may be accomplished either by self-orientation of the stents (such as by interference between features of the stent and a previously implanted stent or valve structure) or by manual orientation of the stent to align its features with anatomical or previous bioprosthetic features, such as can be accomplished using fluoroscopic visualization techniques, for example. For example, when aligning the stents of the invention with native anatomical structures, they should be aligned so as to not block the coronary arteries, and native mitral or tricuspid valves should be aligned relative to the anterior leaflet and/or the trigones/commissures.

The support structures of the stents can be wires formed from a shape memory material such as a nickel titanium alloy (e.g., Nitinol). With shape memory material, the support structure is self-expandable from a contracted state to an expanded state, such as by the application of heat, energy, and the like, or by the removal of external forces (e.g., compressive forces). This support structure can also be repeatedly compressed and re-expanded without damaging the structure of the stent. In addition, the support structure of such an embodiment may be laser cut from a single piece of material or may be assembled from a number of different components. For these types of stent structures, one example of a delivery system that can be used includes a catheter with a retractable sheath that covers the stent until it is to be deployed, at which point the sheath can be retracted to allow the stent to expand.

The stents can alternatively be a series of wires or wire segments arranged so that they are capable of transitioning from a collapsed state to an expanded state with the application or removal of external and/or internal forces. These individual wires comprising the support structure can be formed of a metal or other material. Further, the wires are arranged in such a way that the stent can be folded or compressed to a contracted state in which its internal diameter is considerably smaller than its internal diameter when the structure is in an expanded state. In its collapsed state, such a support structure with an attached valve can be mounted over a delivery device, such as a balloon catheter, for example. The support structure is configured so that it can be changed to its expanded state when desired, such as by the expansion of a balloon catheter or removal of external forces that are provided by a sheath, for example. The delivery systems used for such a stent can be provided with degrees of rotational and axial orientation capabilities in order to properly position the new stent at its desired location.

Referring now to the Figures, wherein the components are labeled with like numerals throughout the several Figures, and initially to FIGS. 1-10, one embodiment of a stent delivery system is illustrated. This system can include a cartridge for initial attachment of a stent and/or stent device to the stent base device and subsequent attachment to the delivery system, thereby providing quick and simple attachment of a stent to a delivery system by an operator. In one embodiment, the attachment mechanism is a dovetail type of connection, which includes a mating feature on both a cartridge and a delivery system that allows the stent to be preloaded to the cartridge and easily attached by the clinician to the delivery system. Other connection means are also contemplated, such as snap-fit connections, threaded connections, clips, pins, magnets, and/or the like. Alternatively, the pigtail delivery system may include more permanently attached components that do not use features of a cartridge-based system.

Figure 22:
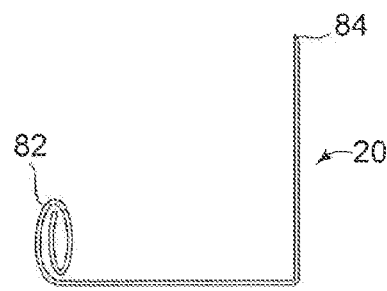
FIG. 22 is a perspective view of one of the wires of a pigtail delivery system of the invention.

One delivery system of the invention can further include a series of wires for connecting the stented valve to the delivery system. In one embodiment, each of the wires can be formed at its distal end into a coiled or "pigtail" configuration. The coiled end of each wire can be secured to a feature of a stent, such as a stent crown, when the wire end is coiled. Straightening the wire can then release the stent feature to which it was secured, as is described below in further detail. One exemplary embodiment of a wire 20 having a coiled distal end 82 and a proximal end 84 is illustrated in FIG. 22. The wire can be bent at approximately a 90 degree angle between the distal end 82 and proximal end 84, or it can be bent at an angle other than 90 degrees, or it can be a straight wire portion with no bend or curves. As shown, the distal end 82 of the wire 20 is shaped to Create approximately 1½ coils or loops; however, the wire 20 may include more or less coils or loops than shown. The wires can be made of a wide variety of materials, such as high tensile strength spring wire material or NiTi, for example. Alternatively, the wire can be somewhat malleable such that it does not necessarily return to the original coil shape once any stented valve features have been released from the wire.

The size and exact configuration of the pigtail end portion of each wire can be chosen or designed so that the forces required to retract and deploy the stent are within a desirable range. The pigtail portion of the wire should be strong enough to prevent inadvertent release from the delivery system during stent positioning, resheathing, repositioning, and/or the like. In addition, the pigtail portion of the wire should be sufficiently flexible that it does not require excessive force to straighten it during implant device deployment. In one exemplary embodiment, the wire 20 is approximately 0.010 inches in diameter, thereby requiring approximately 7 pounds of pull force to uncoil the distal end 82 of the wire 20. However, different materials and different sized wires can be used for the pigtail wires that provide different delivery system properties.

The proximal end 84 of each of the wires 20 is fixed to a hub or base portion that is located on a center lumen of the cartridge or delivery system. The wire 20 can be secured to the hub or base portion using various mechanical methods and/or adhesives. In one embodiment, the coiled or pigtail portions at the distal end 82 are initially coiled around the wires of one end of a stent and then are fully or partially straightened to deploy the stented valve. The wire can be made of spring materials or shape memory materials that may be cured or "set" via a heat treating process so that the coiled wire end can be retracted, clocked, redeployed, disengaged, or the like without the use of additional tools or the management of removed parts. In particular, the wires that have a pigtail portion at their distal ends are retracted relative to one or more tubes in which they are enclosed until the pigtail portions are adjacent to one end of one of the tubes. That is, the wires are pulled relative to the tube(s), the tube(s) are pushed forward relative to the wires, or both the wires and the tubes are moved relative to each other. The diameter of the coil circle or loop can be relatively large in size as compared to the diameter of the tube opening into which they are being pulled so that the coils will contact and interfere with the end of the tube when they are pulled toward it. The wires are then pulled further back into the tube, thereby straightening the pigtail portions until they are released from the stent wires they had been encircling. In one embodiment, interference between the larger area or volume of the pigtail portions and the inner area of the tube forces the pigtail portions to uncoil or straighten as they are pulled into the tube. Alternatively, the coiled diameter of the loops can be relatively small in size as compared to the diameter of the tubes into which they are being pulled (see FIG. 13, for example), so that the stent crown will instead contact and interfere with the end of the tubes when they are pulled toward it. This will inhibit the stent movement so that additional pulling force on the wires will cause the coiled wire end to uncoil.

Figure 2:
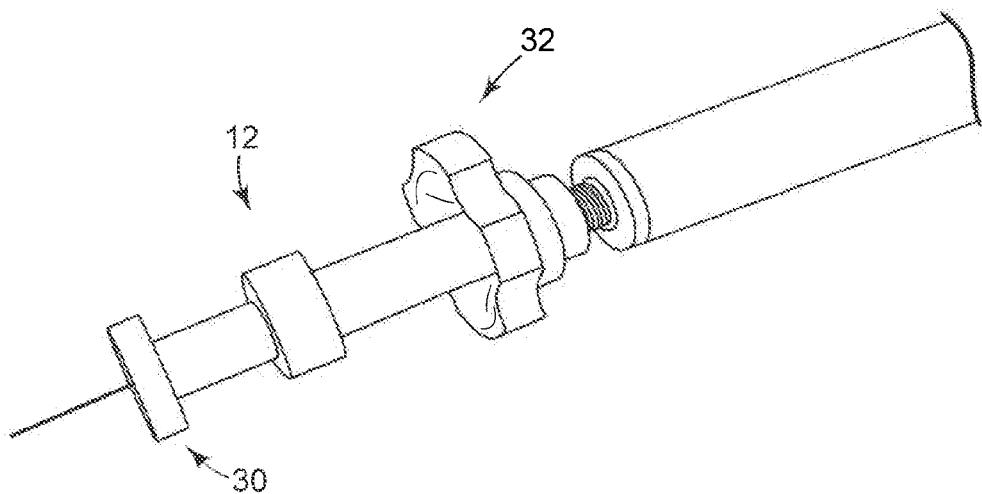
FIG. 2 is a perspective view of a proximal end of the delivery system illustrated in FIG. 1.

In particular, FIG. 1 illustrates one exemplary delivery system 10 for a pigtail type of system that generally includes a proximal end 12 and a distal end 14. FIG. 2 shows an enlarged view of the proximal end 12 of the delivery system 10 of FIG. 1, which includes a first knob 30 and a second knob 32 for use in controlling the delivery and deployment of a stent at the generally distal end 14, as will be described in further detail below. A delivery system for percutaneous stent and valve delivery can comprise a relatively long delivery system that can be maneuvered through a patient's vasculature until a desired anatomical location is reached. In any case, the delivery system can include features that allow it to deliver a stent to a desired location in a patient's body.

Figure 3:
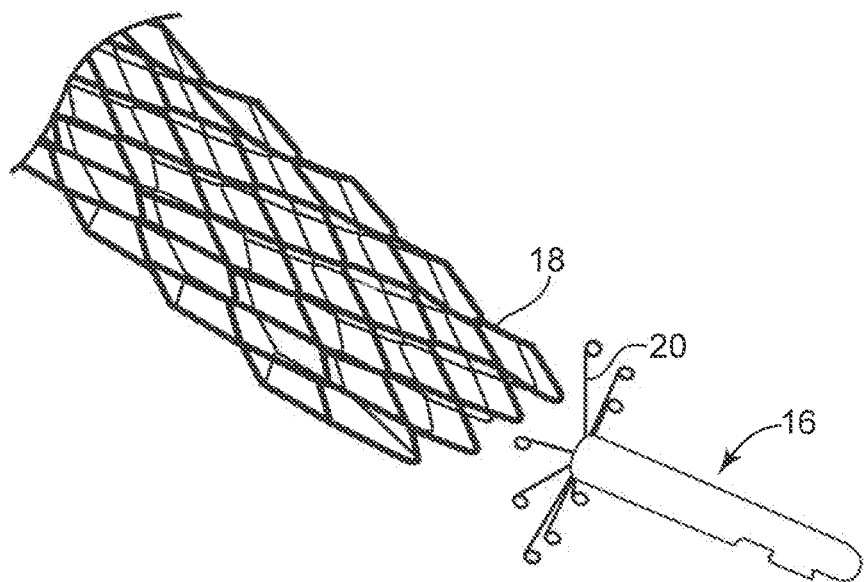
FIG. 3 is a perspective view of a cartridge having plural wires with coiled ends as the wires are being attached to a stent frame.

A cartridge 16 is illustrated in FIG. 3 adjacent to a stent 18 to which it will be attached. The stent 18 is then illustrated in FIG. 4 as attached to the cartridge 16 via the coiled or pigtail ends of the wires 20. That is, the cartridge 16 includes a post 19 having a series of wires 20 extending from one end and a dovetail attachment portion 22 at the opposite end. Each of the wires 20 includes a generally straight portion that is connected to the post 19 at its proximal end 84 and further includes a "pigtail" or curled portion at its distal end 82. Each wire 20 is made of a shape-memory type of material (e.g., Nitinol) such that it can be straightened by applying an external force when in the proximity of a stent to which it will be attached and return generally to its curled configuration when the straightening force is removed. Alternatively, a wire can be used that is permanently deformed when sufficient force has been applied to it to release the stented valve from the delivery system.

Figure 4:
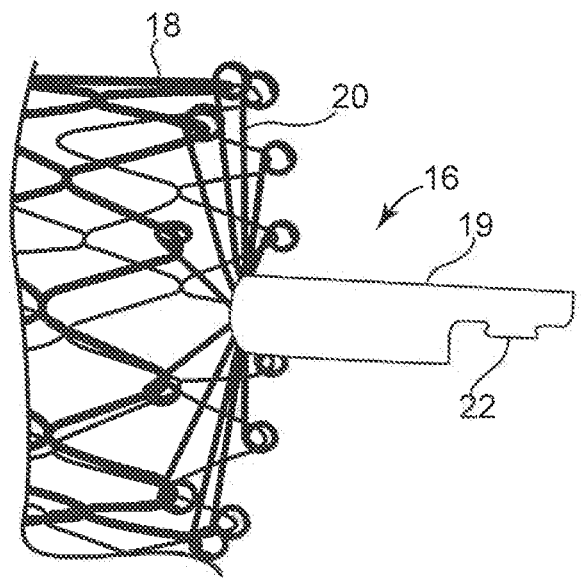
FIG. 4 is an enlarged side view of the cartridge of FIG. 3 attached to the crowns at one end of a stent.

In order to load a stent onto the wires 20 of cartridge 16, the curled end of each wire 20 can be straightened or partially straightened and placed adjacent to one of the crowns or "V" ends of the stent. The force on each wire 20 can then be removed or reduced so that the distal end of the wire coils back toward its pigtail configuration, thereby wrapping around and capturing one crown of the stent 18, as is shown in FIG. 4. Alternatively, a malleable type of wire material can be used, wherein the coil can be formed by wrapping the wire around the stent crown during the stent loading process. If a different stent construction is used, the coiled wires can instead engage with some other feature of that type of stent. The cartridge is preferably provided with the same number of wires having pigtail or coiled wire ends as the number of crowns provided on the corresponding stent, although the cartridge can be provided with more or less wires having coiled ends. It is also contemplated that a single crown of a stent may have more than one pigtail wire attached to it. After the wires 20 of the cartridge 16 are attached to the stent 18, as is illustrated in FIG. 4, the cartridge and stent combination can then be attached to the delivery system 10.

The use of a cartridge with the delivery systems of the invention can provide advantages to the stent loading process. For example, a cartridge and stent can be provided to the clinician with the stent pre-attached to the cartridge so that the clinician does not need to perform the stent attachment step prior to surgery. In addition, the cartridge concept simplifies the attachment of the valve to the delivery system, improves the reliability and consistency of the attachment, and eliminates the chance that the valve will mistakenly be attached backwards onto the delivery system. The exemplary stent 18, one end of which is shown in the Figures, is made of a series of wires that are compressible and expandable through the application and removal of external forces, and may include a series of Nitinol wires that are approximately 0.011-0.015 inches in diameter, for example. That is, the stent 18 may be considered to be a self-expanding stent. However, the stent to which the pigtail wire portions of the invention are attached can have a number of different configurations and can be made of awide variety of different materials. In order to be used with the delivery systems of the invention, however, the stent is preferably designed with at least one point or feature to which a coiled wire end can be attached. That is, while an open-ended type of stent crown is shown, other stent end configurations can alternatively be used, such as eyelets, loops, or other openings.

Figure 5:
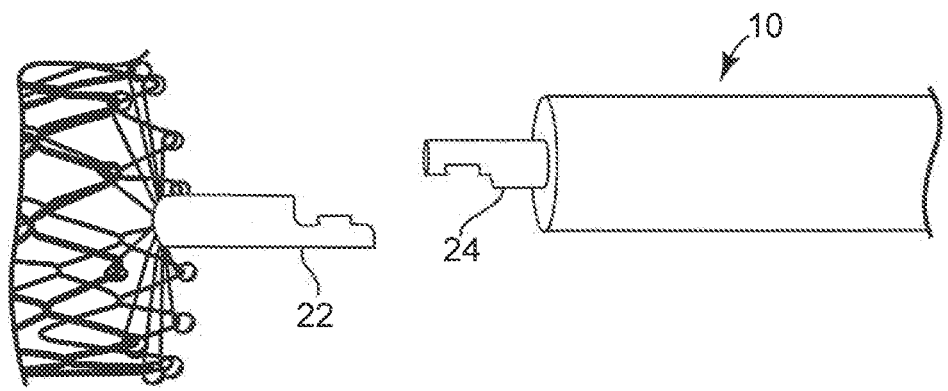
FIG. 5 is a side view of the cartridge and attached stent of FIG. 4 in proximity to a portion of a delivery system to which they will be attached.

FIG. 5 illustrates one end of the delivery system 10 as having a dovetail portion 24 that can mate or attach to a corresponding dovetail attachment portion 22 of the cartridge 16 by positioning the two pieces so that they become engaged with each other. This particular dovetail arrangement is exemplary and it is understood that a different mechanical arrangement of cooperating elements on two portions of a delivery system can instead be used, where the stent structure is attached to one of the pieces of the delivery system, which in turn is mechanically attachable to another piece of the delivery system. It is further contemplated that the wires with pigtail ends are not part of a cartridge-based system, but that the wires are instead attached directly to a delivery system that does not include a cartridge.

Figure 6:
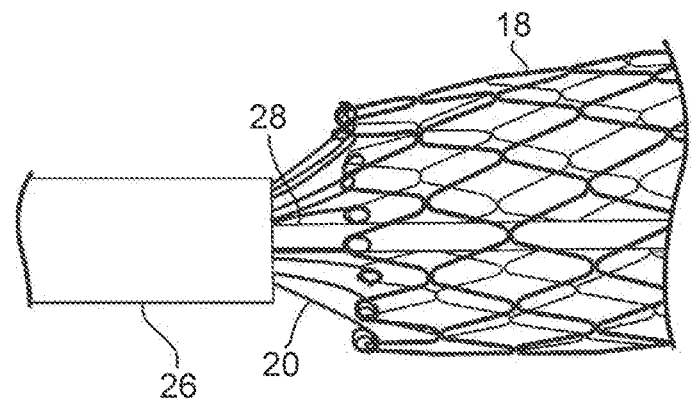
FIG. 6 is a side view of a delivery system of the invention with an attached stent.
Figure 7:
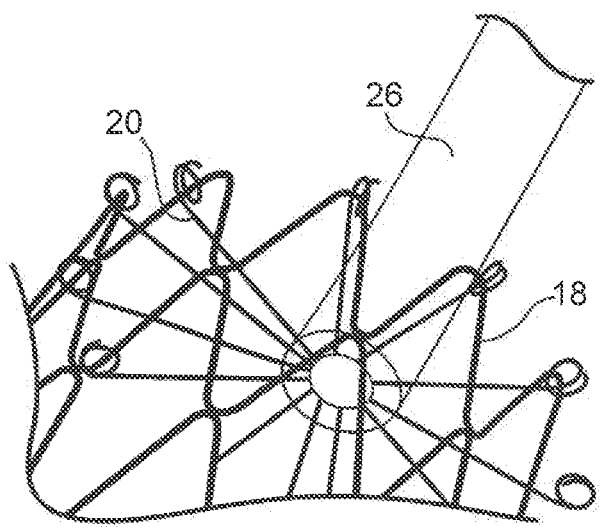
FIG. 7 is an enlarged perspective view of the coiled or pigtail ends of wires of a delivery system attached to a stent.

As shown in FIGS. 6 and 7, after the cartridge 16 is attached to the delivery system 10, the cartridge 16 and its attached stent 18 are then retracted into a hollow tube or lumen 26 of the delivery system by moving or pulling the cartridge 16 toward the proximal end of the delivery device. This movement is continued until the crowns of the stent 18 are adjacent to the end of the lumen 26. It is noted that the lumen 26 may be an outer sheath of the system or that it may be an inner lumen such that another sheath or tube can be positioned on the outside of it. Due to the compressible nature of the stent 18, continued movement of the cartridge 16 toward the proximal end of the delivery device will pull the wires 20 toward a central lumen 28 of the delivery system, thereby also pulling the wires of the stent 18 toward the central lumen 28. The cartridge 16 can then continue to be moved toward the proximal end of the device until the stent 18 is completely enclosed within the lumen 26, as is illustrated in FIG. 1. One exemplary procedure that can be used for such a retraction of the stent 18 into the lumen 26 is to turn the knob 32 (see FIG. 2) in a first direction (e.g., clockwise) until the knob is fully forward. The knob 30 can then be pulled while turning the knob 32 in a second direction that is opposite the first direction (e.g., counter clockwise) until the stent is retracted into the delivery system.

Figure 8:
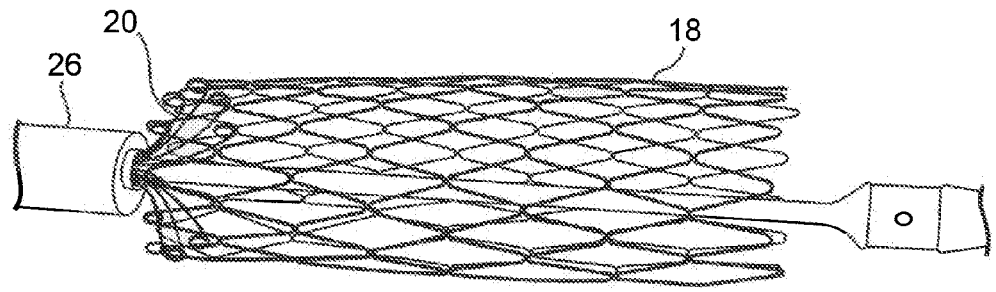
FIGS. 8-10 are side views illustrating various stages of a stent being deployed from a delivery system of the invention.
Figure 9:
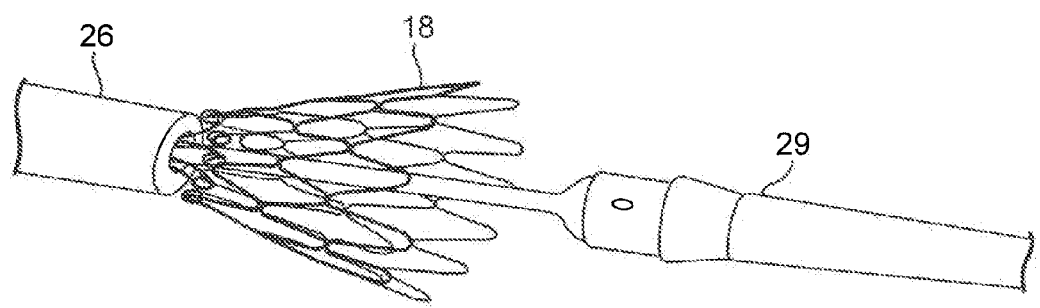
Figure 10:
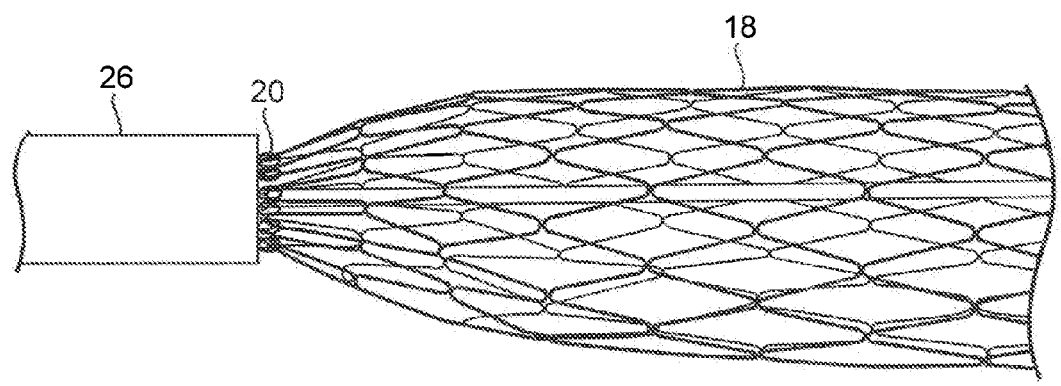

FIGS. 8-10 illustrate the deployment of the stent 18 via a delivery system, which would be initiated once the stent 18 is generally located in its desired anatomic position within a lumen (e.g. heart valve area) of the patient. In particular, FIG. 8 shows the proximal end of a delivery system as the lumen 26 is being moved away from a distal tip 29 of the delivery system, thereby exposing the free end of the stent 18 (i.e., the end of stent 18 that is not attached to the coiled wires 20). In this way, the compressive forces that were provided by enclosing the stent 18 within the lumen 26 are removed and the stent 18 can expand toward its original, expanded condition. FIG. 9 illustrates the next step in the process, where the lumen 26 is moved even further from the distal tip 28 of the system, thereby allowingthe entire length of the stent 18 to be released from the interior portion of lumen 26 for expansion thereof.

In order to release or deploy the stent 18 from the delivery system 10, the wires 20 are then pulled via an actuating mechanism of the delivery system back toward the proximal end of the device until the coiled or pigtail portions are immediately adjacent to the end of the lumen 26, as illustrated in FIG. 10. Next, the cartridge 16 with extending wires 20, along with the lumen 26 to which they are attached, are pulled further toward the proximal end of the device until the coiled ends of the wires 20 contact and interfere with the end, of the lumen 26, which thereby forces the wires 20 to uncoil or straighten at their distal ends. Once the wires 20 are sufficiently straightened or uncoiled, the wires 20 become disengaged from the stent 18, thereby causing the stent 18 to be in its released position within the patient. One exemplary sequence of steps that can be used for such a final deployment of the stent 18 relative to the lumen 26 with this delivery system is to turn knob 32 (see FIG. 2) in a first direction (e.g., clockwise) until the stent is exposed or deployed beyond the lumen 26. Knob 30 can then be retracted, thereby fully releasing the stent 18 from the delivery system.

It is noted that in the above procedure, the stent can be retracted back into the lumen 26 at any point in the process prior to the time that the wires 20 are disengaged from the stent 18, such as for repositioning of the stent if it is determined that the stent is not optimally positioned relative to the patient's anatomy. In this case, the steps described above can be repeated until the desired positioning of the stent is achieved.

In a delivery system that uses the dovetail connection described above or another configuration that allows the stent to be connected to coiled wires of a cartridge, a cartridge can alternatively be pre-attached to a valved stent, packaged together within a gluteraldehyde solution, and provided in this pre-assembled manner to a clinician. In this way, the clinician can simply remove the assembly at the time of the implantation procedure and attach it to the delivery system, which can reduce the amount of time the valved stent needs to be manipulated immediately prior to the time of implantation.

With this system described above, full or partial blood flow through the valve can advantageously be maintained during the period when the stented valve is being deployed into the patient but is not yet released from its delivery system. This feature can, help to prevent complications that may occur when blood flow is stopped or blocked during valve implantation with some other known delivery systems. This also eliminates or reduces the need for additional procedural steps, such as rapid pacing, circulatory assist, and/or other procedures. In addition, it is possible for the clinician to thereby evaluate the opening and closing of leaflets, examine for any paravalvular leakage and evaluate coronary flow and proper positioning of the valve within the target anatomy before final release of the stented valve.

The system and process described above can include simultaneous or generally simultaneous straightening of the wires so that they all uncoil or straighten at their distal ends to disengage from the stent in a single step. However, it is contemplated that the wires can be straightened in a serial manner, where individual wires, pairs of wires, or other combinations of wires are selectively straightened in some predetermined order to sequentially deploy portions of the stent. This can be accomplished either by the structure of the delivery device and/or the structure of the stent and/or through the operation of the delivery system being used.

One exemplary actuating mechanism that can be used with the delivery system can engage all or some of the wires to allow for sequential release of the various stent crowns. This serial release of crowns can be advantageous in that it allows for a high level of control of the diametric deflection (e.g., expansion) of the proximal end of the stented valve. Also, release of high radial force stents sequentially can minimize injury and trauma to the anatomy. Having control of the diametric expansion of all or a portion of the stent can minimize the possibility for device migration, tissue injury and/or embolic events during device deployment. In addition, the serial or sequential release of crowns can require less force for any one wire or set of wires as compared to the amount of force that is required to release all of the wires at the same time. Additionally, regions of the stent such as fixation anchors, petals, and the like could be released in a desired sequent to optimize the positioning and consistency of deployment. Finally, release of specific regions of the stent at different axial zones or regions of varying geometry (inflow flares, bulbous regions, and the like) and/or varying radial force can enable more accurate and stable positioning and device release.

Figure 25:
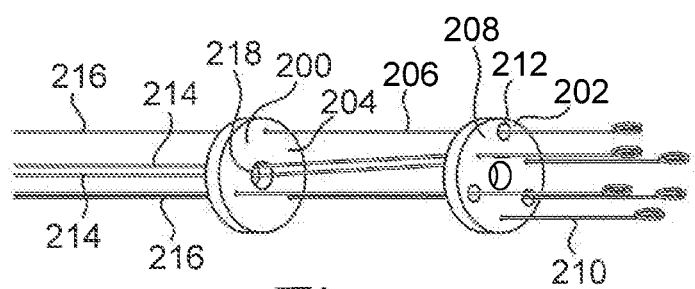
FIG. 25 is a perspective view of a sequential wire release configuration of a stent delivery system.

FIG. 25 illustrates one embodiment of a portion of a sequential wire release configuration of a stent delivery system, which includes a first disk 200 and a second disk 202 spaced from disk 200 generally along the same longitudinal axis. Disk 200 includes a surface 204 from which three wires 206 extend. Disk 202 includes a surface 208 from which three wires 210 extend and three apertures 212 through which the wires 206 of disk 200 can extend. The number of wires and apertures of each disk can be more or less than three, as desired. It is further understood that more than two disks may be provided, with one or more wires being attached to each of the disks. All of the wires 206, 210 terminate at their distal ends with a coiled portion that can include any of the coiled wire properties discussed herein. Each of the wires in the sets of wires 206, 210 can have the same length or a different length so that the coiled ends are at the same or a different distance from the surface 208 of disk 202. This wire release configuration further includes activation members that are shown schematically as wires 214, 216, where wires 214 extend through a center aperture 218 of disk 200 and attach to the disk 202 and wires 216 are attached to the disk 200. The wires 214, 216 can be independently activated to axially move the disks 200 and 202 with their attached wires 210, 206, respectively. The activation wires 214, 216 are intended to be representative activation means, where other activation means can instead be used to provide independent axial movement of the disks 200, 202.

In another embodiment, multiple wires can be released from a stent in a sequence that includes radially releasing stent wires as individual wires, wire pairs, or groups of wires around the periphery of the stent. For example, stent wires on opposite sides of the circumference can be released as a pair, and then the sequence can continue in a clockwise or counterclockwise direction until all of the wires are released from the stent. This can be performed on wires in the same axial plane. It is further advantageous, in accordance with the invention, to sequentially release the wires from the stent among various axial planes. This can be valuable for stents that have varying radial force in planes. In this situation, the delivery systems can include coiled wired ends, for example. Finally, delivery systems of the invention can also be used to release other specific stent features and elements other than or in addition to stent crowns and loops, such as unfurling skirts, dock interface elements, sealing features, barbs, hooks, and the like.

Figure 11:
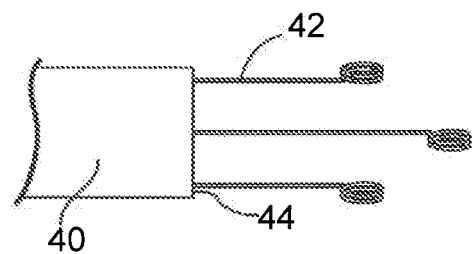
FIG. 11 is a side view of a portion of a delivery system having wires of different lengths with coiled or pigtail ends.

FIG. 11 illustrates one exemplary embodiment of an end portion of a delivery system that includes another embodiment of a lumen 40 from which the distal ends of multiple wires 42 extend. As shown, the distal end of each of the wires 42 has the same number of coils or loops; however, the distance between each of these coils and an end 44 of the lumen 40 is different. Thus, when the wires 42 are attached to a stent and pulled toward an end 44 of the lumen 40, the shortest wire 42 will contact the lumen 40 first. Enough interference is preferably created between the wire 42 and the lumen 40 so that as this shortest wire 42 is pulled into the lumen 40, it is straightened and ultimately released from the stent feature to which it is attached. The wires 42 will continue to be moved further toward the end 44 of lumen 40 until the next longest wire 42 contacts the lumen, which also will be uncoiled or straightened to release it from the stent. This process will be repeated until all of the wires 42 are released from the stent and the stent is fully deployed. Although only three wires 42 are shown in this figure, a different number of wires can instead be provided, and preferably the number of wires provided matches the number of crowns on the stent that is being delivered by the delivery system. In addition, all of the wires can have different lengths and/or numbers of windings at their distal ends, or at least one of the wires can be configured identically to at least one other wire of that delivery system. For example, the delivery system can include identical pairs of wires such that each wire pair releases from a stent simultaneously during the stent deployment process.

Figure 12:
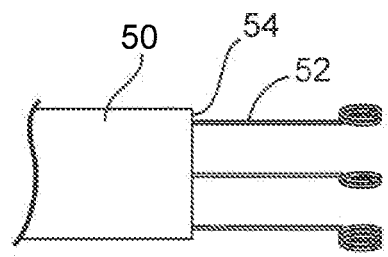
FIG. 12 is a side view of a portion of another delivery system having wires with ends that are coiled to form different numbers of loops.

FIG. 12 illustrates another exemplary embodiment of an end portion of a delivery system that is similar to that of FIG. 11 in that it includes a lumen 50 from which the distal ends of multiple wires 52 extend. Again, the wires 52 are not all configured identically to each other. As shown in this figure, the distal ends of each of the wires 52 has a different number of windings at its coiled end so that when the wires 52 are attached to a stent and pulled toward an end 54 of the lumen 50, the coiled portions of all or most of the wires 52 will contact the end 54 at generally the same time. Continued movement of the wires 52 into the lumen 50 will cause the coiled ends to simultaneously begin straightening or uncoiling; however, the wires 52 with the least number of windings will be completely or almost completely straightened first, thereby releasing these wires from the stent feature to which they were attached. The movement of the wires 52 continues until the wires with the next greater number of windings uncoil and release from the stent and all of the wires 52 are released from the stent so that the stent is fully released. As with the embodiment of FIG. 11, this embodiment provides for a sequential rather than simultaneous release of stent features (e.g., stent crowns). It is noted that more or less than three wires 52 can be used in the system and that all of the wires 52 can be different from each other or that some of the wires 52 can be configured identically (e.g., in wire pairs that release simultaneously).

A distal end of another exemplary embodiment of a delivery system of the invention is illustrated in FIGS. 13-16. This delivery system provides a structure for attachment of a stent or stented valve that allows for full diametric expansion and assessment of the stent or stented valve prior to its release from the delivery system. In this way, the hemodynamic performance, stability, and effect on adjacent anatomical structures (e.g., coronaries, bundle branch, mitral valve interference, etc.) can be assessed and if found to be inadequate or inaccurate, the stent can be recaptured and repositioned before final release of the stent from the delivery system. Alternatively, the entire stent can be removed from a patient before it is released from the delivery system if any undesirable results are obtained during the process of deploying the stent.

Figure 13:
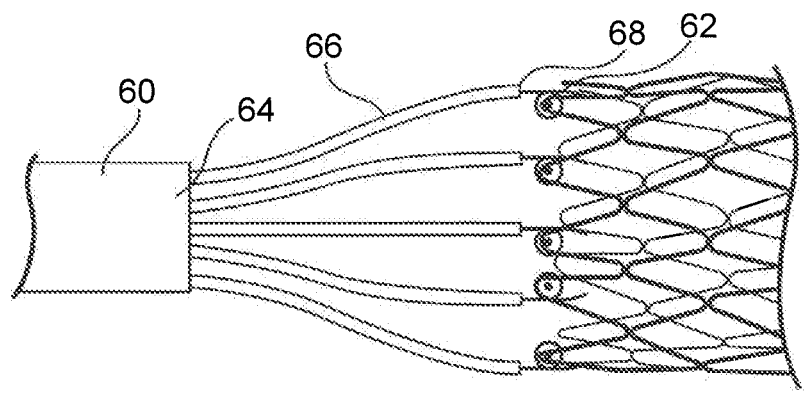
FIG. 13 is a side view of a portion of another delivery system of the invention.
Figure 14:
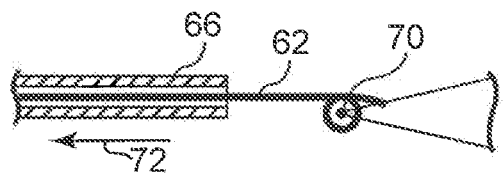
FIGS. 14-16 are sequential cross-sectional side views of a stent crown in various stages of being deployed from the pigtail end of a delivery system of the type illustrated in FIG. 13.
Figure 15:
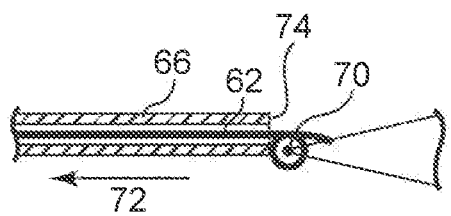
Figure 16:
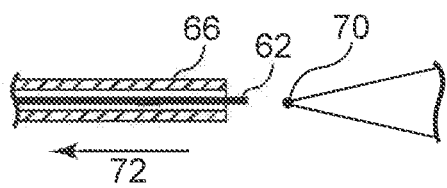

Referring more particularly to FIG. 13, an end portion of a delivery system is shown, which generally includes a lumen 60 having an end 64 from which the distal ends of multiple wires 62 extend. This lumen 60 may be the outer sheath of the delivery system. Each of the wires 62 is partially enclosed within a tube 66, and a coiled end of each of the wires 62 extends beyond a distal end 68 of each of the tubes 66. Each wire 62 is longitudinally moveable or slideable relative to its respective tube 66. The tubes 66 are preferably sized so that when the wires 62 are pulled toward the lumen 60, the coiled ends of the wires 62 will contact and interfere with the ends 68 of the tubes 66. Continued movement of the wires 62 will then cause the wires 62 to straighten until they are released from the stent. These steps are illustrated with a single tube 66 in FIGS. 14-16, which show an extending coiled wire 62 that is attached to (see FIGS. 14 and 15) then detached from (see FIG. 16) a crown 70 of a stent that includes multiple crowns (not shown). In FIG. 14, the wire 62 is coiled around crown 70 of a stent, and then the wire 62 is moved in a direction 72 relative to the tube 66 until the coiled wire portion contacts an end 74 of the tube 66 (see FIG. 15). This will cause interference between the coiled portion of wire 62 and the end 74 of the tube 66. Continued movement of the wire 62 in direction 72 will cause the coiled end of the wire 66 to unfurl. This movement of the wire 62 in direction 72 will be continued until the wire 62 is straightened sufficiently to be released from the crown 70, as shown in FIG. 16.

The tubes 66 are preferably relatively incompressible to allow sufficient tension in the coiled portion of the wires 62 for the wires to straighten when pulled toward the lumen. In other words, the incompressibility of the tubes under tension can simulate flexible columns that resist buckling when the coiled wire ends are pulled against them. In an alternative embodiment of the system of FIG. 13, the wires 62 can have different lengths and/or different numbers of windings in their coils (such as in FIGS. 11 and 12, for example), to provide for sequential release of the wires. In yet another alternative embodiment, the tubes 66 can have different lengths, thereby providing different sizes of gaps between the end of the tubes 66 and the coiled portion of the wires 62.

Figure 23:
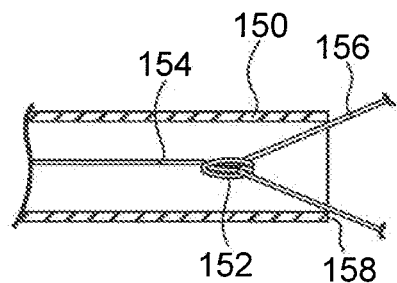
FIG. 23 is a side view of a stent crown positioned relative to an embodiment of a delivery system.
Figure 24:
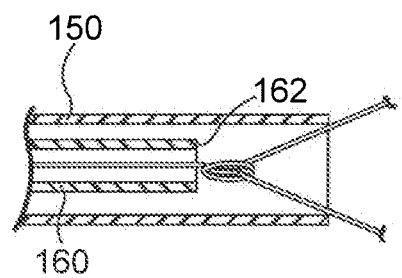
FIG. 24 is a side view of a stent crown positioned relative to another embodiment of a delivery system.

Another alternative stent wire release embodiment is illustrated in FIG. 23 with an end portion of a tube 150 in which a coiled end 152 of a wire 154 is positioned. Coiled end 152 is attached to a stent crown 156 and is at least partially enclosed or contained within the tube 150. In order to detach the wire 154 from the stent crown 156, a retraction force is applied to wire 154 until the stent crown 156 contacts an end 158 of the tube 150, which will limit further movement of the stent. Continued application of force to wire 154 will cause the coiled end 152 to unfurl, thereby releasing the coiled end 152 from the stent crown 156. FIG. 24 illustrates a similar wire release embodiment to that illustrated in FIG. 23, but with an additional tube 160 positioned within tube 150. To release the coiled wire end from the stent crown, the wire can be unfurled by interference between an end 162 of tube 160 and the coiled wire end and/or can be unfurled by movement of the wire relative to the tube 150, as described relative to FIG. 23. It is noted that the wire coils in these and other embodiments of the invention can include a complete or partial coil with multiple windings or a partial winding, depending on the desired release properties.

FIGS. 17-21 illustrate an exemplary delivery system 100 that can be used to provide sequential release of wires that have their coiled ends engaged with a stent 120, where the wires all have generally the same configuration (i.e., length, number of coils, and the like). Delivery system 100 includes a lumen 102 having an end 104 from which the distal ends of multiple wires 106 extend. Each of the wires 106 is partially enclosed within a tube 108. A coiled end 112 of each of the wires 106 extends beyond a distal end 110 of each of the tubes 108. Each wire 106 is longitudinally moveable or slideable relative to its respective tube 108. The tubes 108 are preferably sized so that when the wires 106 are pulled toward the lumen 102 (or when the tubes 108 are moved relative to the wires 106), the coiled ends 112 of the wires 106 will contact the distal ends 110 of the tubes 108. Continued movement of the wires 106 relative to the tubes 108 will then cause the coiled ends 112 of the wires 106 to straighten, thereby facilitating release of the stent 120 from the delivery system 100.

Delivery system 100 further includes a handle 130 from which the lumen 102 extends. The handle 130 includes control aspects for deployment of the stent 120. In particular, handle 130 includes a proximal control knob 132, an intermediate control knob 134, and a distal control knob 136. These control knobs are provided for controlling the delivery and deployment of the stent 120. In one exemplary embodiment of the invention, these knobs are spring-loaded such that they need to be pressed toward the handle in order to move them along a path to a new location. The handle 130 can also be provided with a series of detents that define the specific locations where the knobs can be located. The delivery system 100 may also include additional knobs, levers, or the like that can be used to control the movement of the individual wires 106 or groups of wires.

In order to load a cartridge system to which a stent 120 is attached onto the delivery system 100, the control knobs 132, 134, 136 are moved into a position that can be referred to as the "loading position". Specific detents or other markings can be provided on the delivery system to indicate the correct position for the knobs. The cartridge can then be attached to the delivery system using a dovetail connection or some other type of secure attachment mechanism. The proximal knob 132 can then be moved to a "prepare to sheath position", while the distal knob 136 is moved to the "sheath position". In this way, the sheath will be moved to a position in which the stent is protected by the sheath. The delivery system can then be inserted into the patient in its desired position that facilitates deployment of, the stent. Moving the proximal knob 132 into the "proximal end open position" and the distal knob 136 to the "load position" can then deploy the stent 120. In order to discharge the stent 120, a switch on the delivery system (not shown) or some other control mechanism can be moved into an "open position", the distal knob 136 can be moved to the "discharge position", and the proximal knob 132 can be moved to its "discharge position". The intermediate knob 134 can be manipulated at the same time as the other knobs in order to facilitate the loading, sheathing, deployment, and discharge procedures.

The delivery system 100 further comprises a dual-control procedure and mechanism to sequentially pull the wires 106 into the tubes 108 to disconnect them from the crowns of the stent 120. In this embodiment, a first group of wires 106 can first be removed from the stent 120, and then a second group of wires 106 can be removed from the stent 120 to thereby release the stent 120 from the delivery system 100. Thus, separate mechanisms are provided within the handle 130 to allow a first group of wires 106 to be pulled into the tubes 108 by manipulating one of the control knobs, and then to allow a second group of wires 106 to be pulled into the tubes 108 by manipulating a different control knob. Each of the groups of wires 106 may include half of the wires, or there may be a different percentage of wires 106 in each of the groups. The division of wires into groups may further include having every other wire be included in one group and the alternating wires are included in a second group, although the wires may be grouped in a different pattern. It is further contemplated that additional mechanisms can be provided so that the wires are divided into more than two groups that are controlled by separate mechanisms for sequential wire release.

Figure 17:
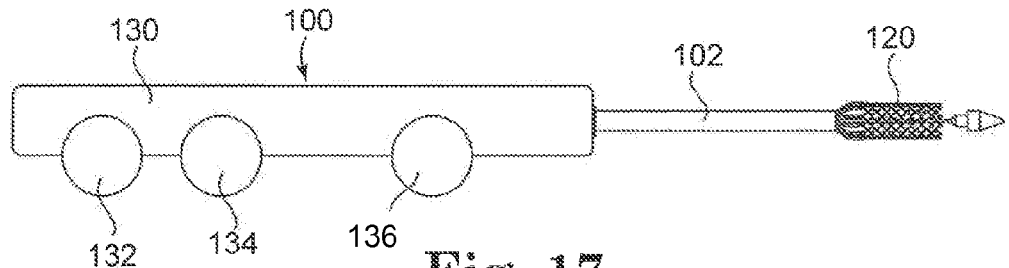
FIG. 17 is a schematic front view of another embodiment of a delivery system of the invention.
Figure 18:
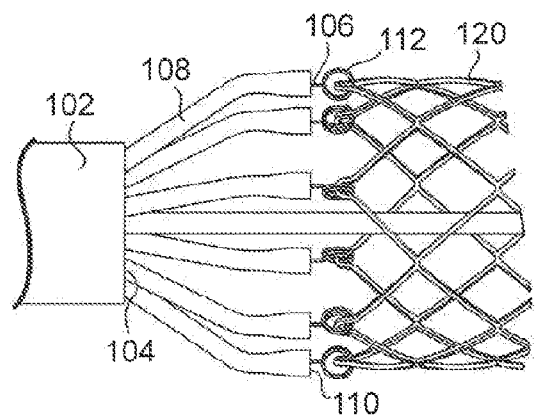
FIG. 18 is an enlarged front view of a portion of the delivery system of FIG. 17, showing plural coiled wires attached to crowns of a stent.
Figure 19:
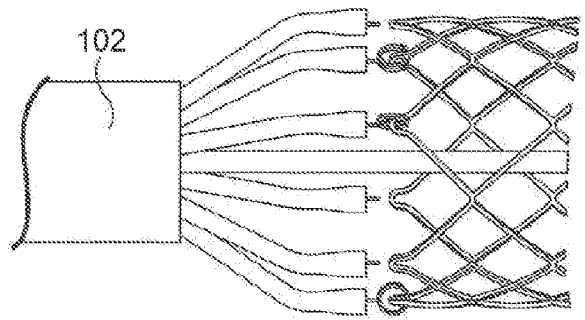
FIG. 19 is an enlarged front view of the same portion of the delivery system shown in FIG. 18, further showing some of the coiled wires detached from the crowns.
Figure 20:
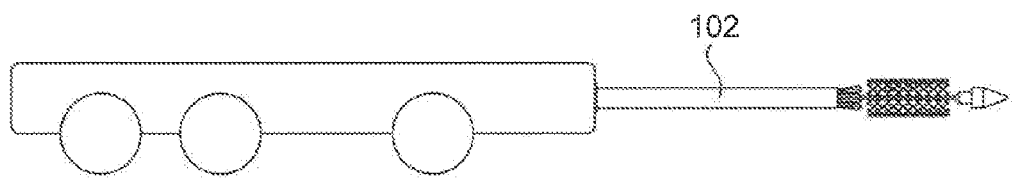
FIG. 20 is a schematic front view of the delivery system of FIG. 17, with the stent detached from all of the coiled wires of the delivery system.
Figure 21:
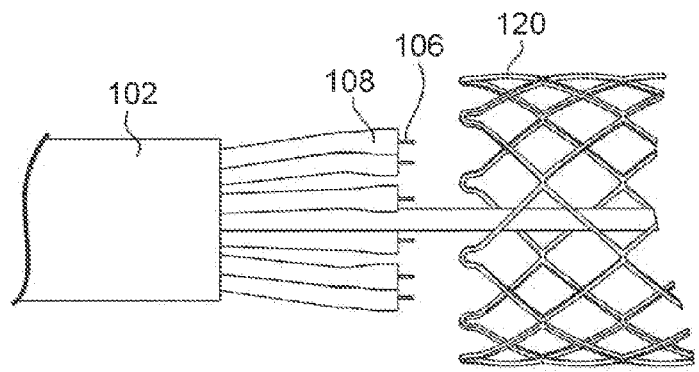
FIG. 21 is an enlarged front view of a portion of the delivery system of FIG. 20.

FIGS. 17 and 18 illustrate the step in which the wires 106 are each attached at their distal end 112 to a crown of stent 120. FIG. 19 illustrates the step in which some of the wires 106 have been pulled into their respective tubes 108, thereby straightening the distal end of the wires and detaching them from the stent 120. However, the remainder of the wires 106 remains attached to the crowns of the stent 120. FIGS. 20 and 21 illustrate the step when the remaining wires 106 have been pulled into their respective tubes 108, thereby straightening the distal end of the wires and detaching them from the stent 120. In this way, the release of the stent 120 from the delivery system 100 is more gradual than when all of the wires are detached from the stent at the same time. The components of the delivery system can alternatively comprise different components than shown to accomplish the serial wire release shown more generally in FIGS. 18, 19, and 21.

The delivery systems of the invention can be used for both apical and transfemoral procedures, for example, and may have the ability to be able to clock the stent, as desired. The delivery systems may further include a removable outer sheath that can accommodate stents of different sizes.

The process of pulling the wires toward the lumen in many of the described embodiments of the invention can be accomplished in a number of ways, such as by rotating the device over coarse threads or pushing a button to slide it to pull the wires toward the lumen. That is, a number of different mechanisms can be used to accomplish this movement of the wires relative to the delivery system. Further, it is noted that while the coiled wire ends described herein are generally shown to be engaging with the end crowns of a stent, the coiled wire ends can instead engage with intermediate stent crowns or other stent features. In addition, although the coiled wire ends are illustrated herein as interfacing with stent crowns that are uniformly provided at the ends of a cylindrical stent, the coiled wire designs described can also accommodate delivery of valved stents that have non-uniform axial or longitudinal stent crowns of stent feature attachment geometries.

The delivery systems of the invention, having a stent attached via coiled wire ends, can be delivered through a percutaneous opening (not shown) in the patient. The implantation location can be located by inserting a guide wire into the patient, which guide wire extends from a distal end of the delivery system. The delivery system is then advanced distally along the guide wire until the stent is positioned relative to the implantation location. In an alternative embodiment, the stent is delivered to an implantation location via a minimally invasive surgical incision (i.e., non-percutaneously). In another alternative embodiment, the stent is delivered via open heart/chest surgery. In one embodiment of the invention, the stent can include a radiopaque, echogenic, or MRI visible material to facilitate visual confirmation of proper placement of the stent. Alternatively, other known surgical visual aids can be incorporated into the stent. The techniques described relative to placement of the stent within the heart can be used both to monitor and correct the placement of the stent in a longitudinal direction relative to the length of the anatomical structure in which it is positioned.

One or more markers on the valve, along with a corresponding imaging system (e.g., echo, MRI, etc.) can be used with the various repositionable delivery systems described herein in order to verify the proper placement of the valve prior to releasing it from the delivery system. A number of factors can be considered, alone or in combination, to verify that the valve is properly placed in an implantation site, where some exemplary factors are as follows: (1) lack of paravalvular leakage around the replacement valve, which can be advantageously examined while blood is flowing through the valve since these delivery systems allow for flow through and around the valve; (2) optimal rotational orientation of the replacement valve relative to the coronary arteries; (3) the presence of coronary flow with the replacement valve in place; (4) correct longitudinal alignment of the replacement valve annulus with respect to the native patient anatomy; (5) verification that the position of the sinus region of the replacement valve does not interfere with native coronary flow; (6) verification that the sealing skirt is aligned with anatomical features to minimize paravalvular leakage; (7) verification that the replacement valve does not induce arrhythmias prior to final release; and (8) verification that the replacement valve does not interfere with function of an adjacent valve, such as the mitral valve.

The present invention has now been described with reference to several embodiments thereof. The entire disclosure of any patent or patent application identified herein is hereby incorporated by reference. The foregoing detailed description and examples have been given for clarity of understanding only. No unnecessary limitations are to be understood therefrom. It will be apparent to those skilled in the art that many changes can be made in the embodiments described without departing from the scope of the invention. Thus, the scope of the present invention should not be limited to the structures described herein, but only by the structures described by the language of the claims and the equivalents of those structures.

What is claimed is:

1. A delivery system for delivering an implantable stented device into a body lumen, the delivery system comprising:
    a tubular body having a proximal end and a distal end;
    a plurality of activation members extending from the distal end of the tubular body; and
    a first disk comprising:
        a proximal surface;
        a distal surface;
        at least one stent engagement element attached to the distal surface of the first disk; and
        an aperture; and
    a second disk comprising:
        a proximal surface;
        a distal surface;
        at least one stent engagement element attached to the distal surface of the second disk; and
        an aperture,
    wherein at least one activation member attaches to the proximal surface of the first disk,
    wherein at least one activation member passes through the aperture of the first disk and attaches to the proximal surface of the second disk, and
    wherein at least one stent engagement element attached to the distal surface of the first disk passes through the aperture of the second disk.

2. The delivery system of claim 1, wherein the first and second disks are generally along the same longitudinal axis.

3. The delivery system of claim 1, wherein a distal end each stent engagement element comprises a coiled portion.

4. The delivery system of claim 3, wherein each of the coiled portions has the same number of coils.

5. The delivery system of claim 3, wherein the coiled portion of at least one of the stent engagement elements has a different number of coils than the other stent engagement elements.

6. The delivery system of claim 3, wherein an outer diameter of the coiled portion of each stent engagement element passing through the aperture of the second disk is larger than the diameter of the aperture through which the stent engagement element passes, such that the stent engagement element cannot be moved axially through its respective aperture when in its coiled configuration.

7. The delivery system of claim 6, wherein the stent engagement element of each stent engagement element passing through the aperture of the second disk can be moved axially through its respective aperture when in its uncoiled configuration.

8. The delivery system of claim 3, wherein each stent engagement element can be at least temporarily deformed for engagement and disengagement with a stent crown of an implantable stented device.

9. The delivery system of claim 1, wherein each of the stent engagement elements has the same length.

10. The delivery system of claim 1, wherein at least one of the stent engagement elements has a different length than the other stent engagement elements.

11. The delivery system of claim 1, wherein the stent engagement elements are wires.

12. The delivery system of claim 1, wherein the activation members are wires.

13. The delivery system of claim 1, wherein the aperture of the first disk is centered about a longitudinal axis of the first disk.

14. The delivery system of claim 1, wherein the activation members are independently activated to axially move the first and second disks relative to each other.

15. The delivery system of claim 1, further comprising a sheath positioned at least partially around the activation members and the disks.

16. A sequential release mechanism for deploying an implantable stented device into a body lumen, the sequential release mechanism comprising:
 a plurality of activation members;
 a first disk comprising:
  a proximal surface;
  a distal surface;
  at least one stent engagement element attached to the distal surface of the first disk; and
  an aperture; and
 a second disk comprising:
  a proximal surface;
  a distal surface;
  at least one stent engagement element attached to the distal surface of the second disk; and
 an aperture,
 wherein at least one activation member attaches to the proximal surface of the first disk,
 wherein at least one activation member passes through the aperture of the first disk and attaches to the proximal surface of the second disk, and
 wherein at least one stent engagement element attached to the distal surface of the first disk passes through the aperture of the second disk.

17. The sequential release mechanism of claim 16, wherein a distal end of each stent engagement element comprises a coiled portion.

18. The sequential release mechanism of claim 16, wherein the activation members are independently activated to axially move the first and second disks relative to each other.

19. The sequential release mechanism of claim 16, wherein each stent engagement element can be at least temporarily deformed for engagement and disengagement with a stent crown of an implantable stented device.

20. A method of deploying an implantable stented device with a delivery system that comprises:
 a tubular body having a proximal end and a distal end;
 a plurality of activation members extending from the distal end of the tubular body; and
 a first disk comprising:
  a proximal surface;
  a distal surface;
  at least one stent engagement element attached to the distal surface of the first disk; and
  an aperture; and
 a second disk comprising:
  a proximal surface;
  a distal surface;
  at least one stent engagement element attached to the distal surface of the second disk; and
 an aperture,
 wherein at least one activation member attaches to the proximal surface of the first disk,
 wherein at least one activation member passes through the aperture of the first disk and attaches to the proximal surface of the second disk, and
 wherein at least one stent engagement element attached to the distal surface of the first disk passes through the aperture of the second disk,
 the method comprising:
 engaging the stent engagement elements with a proximal end of the implantable stented device,
 positioning the implantable stented device at an implantation location within a body lumen,
 proximally moving at least one activation member, thereby proximally moving at least one disk, such that at least one stent engagement element disengages from the implantable stented device.

21. The method of claim 20, wherein proximally moving at least one activation member comprises:
 proximally moving a first activation member or a first set of activation members, thereby moving the first disk, such that the at least one stent engagement elements attached to the first disk disengage from the implantable stented device; and
 proximally moving a second activation member or a second set of activation members, thereby moving the second disk, such that the at least one stent engagement elements attached to the second disk disengage from the implantable stented device.

22. The method of claim of 21, wherein by proximally moving the first disk, the at least one stent engagement elements attached to the distal surface of the first disk contact the second disk and are at least temporarily deformed, allowing the at least one stent engagement elements to disengage from the implantable stented device and pass through the respective aperture of the second disk.

23. The method of claim 21, wherein the second disk is sequentially moved first, and the first disk is sequentially moved second.

* * * * *